(12) United States Patent
Donovan et al.

(10) Patent No.: US 8,481,289 B2
(45) Date of Patent: Jul. 9, 2013

(54) TRIPLE ACTING ANTIMICROBIALS THAT ARE REFRACTORY TO RESISTANCE DEVELOPMENT

(75) Inventors: David M. Donovan, Baltimore, MD (US); Stephen C. Becker, Baltimore, MD (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 665 days.

(21) Appl. No.: 12/460,812

(22) Filed: Jul. 24, 2009

(65) Prior Publication Data

US 2010/0158886 A1 Jun. 24, 2010

Related U.S. Application Data

(60) Provisional application No. 61/135,810, filed on Jul. 24, 2008.

(51) Int. Cl.
*C12P 21/04* (2006.01)

(52) U.S. Cl.
USPC .................................................. 435/69.7

(58) Field of Classification Search
None
See application file for complete search history.

(56) References Cited

U.S. PATENT DOCUMENTS 7,572,602 B1 * 8/2009 Donovan ................. 435/69.7

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*

* cited by examiner

*Primary Examiner* — Sheridan Swope
(74) *Attorney, Agent, or Firm* — John D. Fado; Evelyn M. Rabin

(57) ABSTRACT

Multi-drug resistant superbugs are a persistent problem in modern health care. This invention provides an antimicrobial endolysin-Lysostaphin triple fusion protein, comprising (1) an endolysin CHAP endopeptidase domain, (2) an endolysin amidase domain, and (3) a Lysostaphin glycyl-glycine endopeptidase domain. The domains are derived from two proteins that show antimicrobial synergy when used in combination. The protein has specificity and exolytic activity for the peptidoglycan cell wall of untreated, live *Staphylococcus aureus* from many growth phases i.e. stationary, logarithmic and biofilm growth. The recombinant triple fusion protein comprising the three functional antimicrobial domains is designed to be refractory to resistance development.

10 Claims, 9 Drawing Sheets
(5 of 9 Drawing Sheet(s) Filed in Color)

SEQUENCE LISTING

```
<160> NUMBER OF SEQ ID NOS: 35

<210> SEQ ID NO 1
<211> LENGTH: 768
<212> TYPE: DNA
<213> ORGANISM: Staphylococcus simulans

<400> SEQUENCE: 1
atggctgcaa cacatgaaca ttcagcacaa tggttgaata attacaaaaa aggatatggt      60
tacggccctt atccattagg tataaatggc ggtatgcact acggagttga tttttttatg     120
aatattggaa caccagtaaa agctatttca agcggaaaaa tagttgaagc tggttggagt     180
aattacggag gaggtaatca aataggtctt attgaaaatg atggagtgca tagacaatgg     240
tatatgcatc taagtaaata taatgttaaa gtaggagatt atgtcaaagc tggtcaaata     300
atcggttggt ctggaagcac tggttattct acagcaccac atttacactt ccaaagaatg     360
gttaactcat tttcacagtc aactgcccaa gatccaatgc ctttcttaaa gagcgcagga     420
```

-continued

```
tatggaaaag caggtggtac agtaactcca acgccgaata caggttggaa aacaaacaaa    480
tatggcacac tatataaatc agagtcagct agcttcacac ctaatacaga tataataaca    540
agaacgactg gtccatttag aagcatgccg cagtcaggag tcttaaaagc aggtcaaaca    600
attcattatg atgaagtgat gaaacaagac ggtcatgttt gggtaggtta tacaggtaac    660
agtggccaac gtatttactt gcctgtgaga acatggcaga agtctactaa tactctgggt    720
gttctgtggg gaactataaa gctcgagcac caccaccacc accactga                 768
```

<210> SEQ ID NO 2
<211> LENGTH: 255
<212> TYPE: PRT
<213> ORGANISM: Staphylococcus simulans

<400> SEQUENCE: 2

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
                20                  25                  30

His Tyr Gly Val Asp Phe Phe Met Asn Ile Gly Thr Pro Val Lys Ala
            35                  40                  45

Ile Ser Ser Gly Lys Ile Val Glu Ala Gly Trp Ser Asn Tyr Gly Gly
        50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Gln Ser Thr
        115                 120                 125

Ala Gln Asp Pro Met Pro Phe Leu Lys Ser Ala Gly Tyr Gly Lys Ala
    130                 135                 140

Gly Gly Thr Val Thr Pro Thr Pro Asn Thr Gly Trp Lys Thr Asn Lys
145                 150                 155                 160

Tyr Gly Thr Leu Tyr Lys Ser Glu Ser Ala Ser Phe Thr Pro Asn Thr
                165                 170                 175

Asp Ile Ile Thr Arg Thr Thr Gly Pro Phe Arg Ser Met Pro Gln Ser
            180                 185                 190

Gly Val Leu Lys Ala Gly Gln Thr Ile His Tyr Asp Glu Val Met Lys
        195                 200                 205

Gln Asp Gly His Val Trp Val Gly Tyr Thr Gly Asn Ser Gly Gln Arg
    210                 215                 220

Ile Tyr Leu Pro Val Arg Thr Trp Gln Lys Ser Thr Asn Thr Leu Gly
225                 230                 235                 240

Val Leu Trp Gly Thr Ile Lys Leu Glu His His His His His
                245                 250                 255
```

<210> SEQ ID NO 3
<211> LENGTH: 1512
<212> TYPE: DNA
<213> ORGANISM: artificial sequence
<220> FEATURE:
<223> OTHER INFORMATION: Phage K

<400> SEQUENCE: 3

```
atggctaaga ctcaagcaga aataaataaa cgtttagatg cttatgcaaa aggaacagta    60
```

```
gatagccctt acagagttaa aaaagctaca agttatgacc catcatttgg tgtaatggaa    120
gcaggagcca ttgatgcaga tggttactat cacgctcagt gtcaagacct tattacagac    180
tatgttttat ggttaacaga taataaagtt agaacttggg gtaatgctaa agaccaaatt    240
aaacagagtt atggtactgg atttaaaata catgaaaata aaccttctac tgtacctaaa    300
aaaggttgga ttgcggtatt tacatccggt agttatgaac agtggggtca cataggtatt    360
gtatatgatg gaggtaatac ttctacattt actattttag agcaaaactg gaatggttat    420
gctaataaaa aacctacaaa acgtgtagat aattattacg gattaactca cttcattgaa    480
atacctgtaa aagcaggaac tactgttaaa aaagaaacag ctaagaaaag cgcaagtaaa    540
acgcctgcac ctaaaaagaa agcaacacta aaagtttcta agaatcacat taactataca    600
atggataaac gtggtaaaaa acctgaagga atggtaatac acaacgatgc aggtcgttct    660
tcaggacaac aatacgagaa ttcattagct aatgcaggtt atgctagata cgctaatggt    720
attgctcatt actacggctc tgaaggttat gtatgggaag caatagatgc taagaatcaa    780
attgcttggc acacgggtga tggaacagga gcaaactcag gtaactttag atttgcaggt    840
attgaagtct gtcaatcaat gagtgctagt gatgctcaat tccttaaaaa tgaacaagca    900
gtattccaat ttacagcaga gaaatttaaa gaatggggtc ttactcctaa ccgtaaaact    960
gtaagattgc atatggaatt tgtaccaact gcctgtcctc accgttctat ggttcttcat   1020
acaggattta atccagtaac acaaggaaga ccatcacaag caataatgaa taaattaaaa   1080
gattatttca ttaaacaaat taaaaactac atggataaag aacttcaag ttctacagta   1140
gttaaagatg gtaaaacaag tagcgcaagt acaccggcaa ctagaccagt tacaggttct   1200
tggaaaaaga accagtacgg aacttggtat aaaccgaaaa atgcaacatt tgtcaatggt   1260
aaccaaccta tagtaactag aataggttct ccattcttaa atgctccagt aggcggtaac   1320
ttaccggcag gggctacaat tgtatatgac gaagtttgta tccaagcagg tcacatttgg   1380
ataggttata atgcttacaa cggtaacaga gtatattgcc ctgttagaac ttgtcaaggt   1440
gttccaccta tcaaatacc tggcgttgcc tggggagtat tcaaactcga gcaccaccac   1500
caccaccact ga                                                       1512
```

<210> SEQ ID NO 4
<211> LENGTH: 503
<212> TYPE: PRT
<213> ORGANISM: artificial sequence
<220> FEATURE:
<223> OTHER INFORMATION: Phage K

<400> SEQUENCE: 4

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr

```
            100                 105                 110
Glu Gln Trp Gly His Ile Gly Ile Val Tyr Asp Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Val Lys Asp Gly
    370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
    450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys Leu
                485                 490                 495

Glu His His His His His
            500

<210> SEQ ID NO 5
<211> LENGTH: 2256
```

```
<212> TYPE: DNA
<213> ORGANISM: artificial sequence
<220> FEATURE:
<223> OTHER INFORMATION: Phage K & Staphylococcus simulans

<400> SEQUENCE: 5
atggctaaga ctcaagcaga aataaataaa cgtttagatg cttatgcaaa aggaacagta      60
gatagccctt acagagttaa aaaagctaca agttatgacc catcatttgg tgtaatggaa     120
gcaggagcca ttgatgcaga tggttactat cacgctcagt gtcaagacct tattacagac     180
tatgttttat ggttaacaga taataaagtt agaacttggg gtaatgctaa agaccaaatt     240
aaacagagtt atggtactgg atttaaaata catgaaaata aaccttctac tgtacctaaa     300
aaaggttgga ttgcggtatt tacatccggt agttatgaac agtggggtca cataggtatt     360
gtatatgatg gaggtaatac ttctacattt actattttag agcaaaactg gaatggttat     420
gctaataaaa aacctacaaa acgtgtagat aattattacg gattaactca cttcattgaa     480
atacctgtaa aagcaggaac tactgttaaa aagaaacag ctaagaaaag cgcaagtaaa      540
acgcctgcac ctaaaaagaa agcaacacta aaagtttcta agaatcacat taactataca     600
atggataaac gtggtaaaaa acctgaagga atggtaatac acaacgatgc aggtcgttct     660
tcaggacaac aatacgagaa ttcattagct aatgcaggtt atgctagata cgctaatggt     720
attgctcatt actacggctc tgaaggttat gtatgggaag caatagatgc taagaatcaa     780
attgcttggc acacgggtga tggaacagga gcaaactcag gtaactttag atttgcaggt     840
attgaagtct gtcaatcaat gagtgctagt gatgctcaat ccttaaaaa tgaacaagca      900 gtattccaat ttacagcaga gaaatttaaa gaatgggggtc ttactcctaa ccgtaaaact    960
gtaagattgc atatggaatt tgtaccaact gcctgtcctc accgttctat ggttcttcat    1020
acaggattta atccagtaac acaaggaaga ccatcacaag caataatgaa taaattaaaa    1080
gattatttca ttaaacaaat taaaaactac atggataaag aacttcaag ttctacagta     1140 gttaaagatg gtaaaacaag tagcgcaagt acaccggcaa ctagaccagt tacaggttct    1200
tggaaaaaga accagtacgg aacttggtat aaaccgaaaa atgcaacatt tgtcaatggt    1260
aaccaaccta gtaactag aataggttct ccattcttaa atgctccagt aggcggtaac     1320
ttaccggcag gggctacaat tgtatatgac gaagtttgta ccaagcagg tcacatttgg     1380 ataggttata atgcttacaa cggtaacaga gtatattgcc ctgttagaac ttgtcaaggt    1440
gttccaccta atcaaatacc tggcgttgcc tggggagtat tcaaactcga cgctgcaaca    1500
catgaacatt cagcacaatg gttgaataat tacaaaaaag gatatggtta cggcccttat    1560
ccattaggta taaatggcgg tatgcactac ggagttgatt ttttatgaa tattggaaca     1620 ccagtaaaag ctatttcaag cggaaaaata gttgaagctg gttggagtaa ttacggagga    1680
ggtaatcaaa taggtcttat tgaaaatgat ggagtgcata gacaatggta tatgcatcta    1740
agtaaatata atgttaaagt aggagattat gtcaaagctg gtcaaataat cggttggtct    1800
ggaagcactg gttattctac agcaccacat ttacacttcc aaagaatggt taactcattt    1860
tcacagtcaa ctgcccaaga tccaatgcct ttcttaaaga gcgcaggata tggaaaagca    1920
ggtggtacag taactccaac gccgaataca ggttggaaaa caaacaaata tggcacacta    1980
tataaatcag agtcagctag cttcacacct aatacagata taataacaag aacgactggt    2040
ccatttagaa gcatgccgca gtcaggagtc ttaaaagcag gtcaaacaat tcattatgat    2100
gaagtgatga aacaagacgg tcatgtttgg gtaggttata caggtaacag tggccaacgt    2160
atttacttgc ctgtgagaac atggcagaag tctactaata ctctggggtgt tctgtgggga    2220
```
actataaagc tcgagcacca ccaccaccac cactga                                    2256

<210> SEQ ID NO 6
<211> LENGTH: 751
<212> TYPE: PRT
<213> ORGANISM: artificial sequence
<220> FEATURE:
<223> OTHER INFORMATION: Phage K & Staphylococcus simulans

<400> SEQUENCE: 6

Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys

```
                    355                 360                 365
Asn Tyr Met Asp Lys Gly Thr Ser Ser Thr Val Val Lys Asp Gly
370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
            405                 410                 415

Phe Val Asn Gly Asn Gln Pro Ile Val Thr Arg Ile Gly Ser Pro Phe
        420                 425                 430

Leu Asn Ala Pro Val Gly Gly Asn Leu Pro Ala Gly Ala Thr Ile Val
    435                 440                 445

Tyr Asp Glu Val Cys Ile Gln Ala Gly His Ile Trp Ile Gly Tyr Asn
450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys Leu
            485                 490                 495

Asp Ala Ala Thr His Glu His Ser Ala Gln Trp Leu Asn Asn Tyr Lys
        500                 505                 510

Lys Gly Tyr Gly Tyr Gly Pro Tyr Pro Leu Gly Ile Asn Gly Gly Met
    515                 520                 525

His Tyr Gly Val Asp Phe Phe Met Asn Ile Gly Thr Pro Val Lys Ala
530                 535                 540

Ile Ser Ser Gly Lys Ile Val Glu Ala Gly Trp Ser Asn Tyr Gly Gly
545                 550                 555                 560

Gly Asn Gln Ile Gly Leu Ile Glu Asn Asp Gly Val His Arg Gln Trp
            565                 570                 575

Tyr Met His Leu Ser Lys Tyr Asn Val Lys Val Gly Asp Tyr Val Lys
        580                 585                 590

Ala Gly Gln Ile Ile Gly Trp Ser Gly Ser Thr Gly Tyr Ser Thr Ala
    595                 600                 605

Pro His Leu His Phe Gln Arg Met Val Asn Ser Phe Ser Gln Ser Thr
610                 615                 620

Ala Gln Asp Pro Met Pro Phe Leu Lys Ser Ala Gly Tyr Gly Lys Ala
625                 630                 635                 640

Gly Gly Thr Val Thr Pro Thr Pro Asn Thr Gly Trp Lys Thr Asn Lys
            645                 650                 655

Tyr Gly Thr Leu Tyr Lys Ser Glu Ser Ala Ser Phe Thr Pro Asn Thr
        660                 665                 670

Asp Ile Ile Thr Arg Thr Thr Gly Pro Phe Arg Ser Met Pro Gln Ser
    675                 680                 685

Gly Val Leu Lys Ala Gly Gln Thr Ile His Tyr Asp Glu Val Met Lys
690                 695                 700

Gln Asp Gly His Val Trp Val Gly Tyr Thr Gly Asn Ser Gly Gln Arg
705                 710                 715                 720

Ile Tyr Leu Pro Val Arg Thr Trp Gln Lys Ser Thr Asn Thr Leu Gly
            725                 730                 735

Val Leu Trp Gly Thr Ile Lys Leu Glu His His His His His His
        740                 745                 750

<210> SEQ ID NO 7
<211> LENGTH: 1941
<212> TYPE: DNA
<213> ORGANISM: artificial sequence
<220> FEATURE:
```

<223> OTHER INFORMATION: Phage K & Staphylococcus simulans

<400> SEQUENCE: 7

```
atggctaaga ctcaagcaga aataaataaa cgtttagatg cttatgcaaa aggaacagta      60
gatagccctt acagagttaa aaaagctaca agttatgacc catcatttgg tgtaatggaa     120
gcaggagcca ttgatgcaga tggttactat cacgctcagt gtcaagacct tattacagac     180
tatgttttat ggttaacaga taataaagtt agaacttggg gtaatgctaa agaccaaatt     240
aaacagagtt atggtactgg atttaaaata catgaaaata aaccttctac tgtacctaaa     300
aaaggttgga ttgcggtatt tacatccggt agttatgaac agtggggtca cataggtatt     360
gtatatgatg gaggtaatac ttctacattt actatttag agcaaaactg gaatggttat      420
gctaataaaa aacctacaaa acgtgtagat aattattacg gattaactca cttcattgaa     480
atacctgtaa aagcaggaac tactgttaaa aaagaaacag ctaagaaaag cgcaagtaaa     540
acgcctgcac ctaaaaagaa agcaacacta aaagtttcta agaatcacat taactataca     600
atggataaac gtggtaaaaa acctgaagga atggtaatac acaacgatgc aggtcgttct     660
tcaggacaac aatacgagaa ttcattagct aatgcaggtt atgctagata cgctaatggt     720
attgctcatt actacggctc tgaaggttat gtatgggaag caatagatgc taagaatcaa     780
attgcttggc acacgggtga tggaacagga gcaaactcag gtaactttag atttgcaggt     840
attgaagtct gtcaatcaat gagtgctagt gatgctcaat tccttaaaaa tgaacaagca     900
gtattccaat ttcagcagaa gaatttaaa gaatggggtc ttactcctaa ccgtaaaact      960
gtaagattgc atatggaatt tgtaccaact gcctgtcctc accgttctat ggttcttcat    1020
acaggattta atccagtaac acaaggaaga ccatcacaag caataatgaa taaattaaaa    1080
gattatttca ttaaacaaat taaaaactac atggataaag gaacttcaag ttctacagta    1140
gttaaagatg gtaaaacaag tagcgcaagt ctcgacgctg caacacatga acattcagca    1200
caatggttga ataattacaa aaaaggatat ggttacggcc cttatccatt aggtataaat    1260
ggcggtatgc actacggagt tgattttttt atgaatattg gaacaccagt aaaagctatt    1320
tcaagcggaa aaatagttga agctggttgg agtaattacg gaggaggtaa tcaaataggt    1380
cttattgaaa atgatggagt gcatagacaa tggtatatgc atctaagtaa atataatgtt    1440
aaagtaggag attatgtcaa agctggtcaa ataatcggtt ggtctggaag cactggttat    1500
tctacagcac acatttaca cttccaaaga atggttaact cattttcaca gtcaactgcc     1560
caagatccaa tgcctttctt aaagagcgca ggatatggaa aagcaggtgg tacagtaact    1620
ccaacgccga atacaggttg gaaaacaaac aaatatggca cactatataa atcagagtca    1680
gctagcttca cacctaatac agatataata acaagaacga ctggtccatt tagaagcatg    1740
ccgcagtcag gagtcttaaa agcaggtcaa acaattcatt atgatgaagt gatgaaacaa    1800
gacggtcatg tttgggtagg ttatacaggt aacagtggcc aacgtattta cttgcctgtg    1860
agaacatggc agaagtctac taatactctg ggtgttctgt ggggaactat aaagctcgag    1920
caccaccacc accaccactg a                                             1941
```

<210> SEQ ID NO 8
<211> LENGTH: 646
<212> TYPE: PRT
<213> ORGANISM: artificial sequence
<220> FEATURE:
<223> OTHER INFORMATION: Phage K & Staphylococcus simulans

<400> SEQUENCE: 8

-continued

```
Met Ala Lys Thr Gln Ala Glu Ile Asn Lys Arg Leu Asp Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
            115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
                180                 185                 190

Ser Lys Asn His Ile Asn Tyr Thr Met Asp Lys Arg Gly Lys Lys Pro
    195                 200                 205

Glu Gly Met Val Ile His Asn Asp Ala Gly Arg Ser Ser Gly Gln Gln
    210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
    275                 280                 285

Ala Ser Asp Ala Gln Phe Leu Lys Asn Glu Gln Ala Val Phe Gln Phe
    290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Lys Asp Gly
    370                 375                 380                Gly

Lys Thr Ser Ser Ala Ser Leu Asp Ala Ala Thr His Glu His Ser Ala
385                 390                 395                 400

Gln Trp Leu Asn Asn Tyr Lys Lys Gly Tyr Gly Tyr Gly Pro Tyr Pro
                405                 410                 415

Leu Gly Ile Asn Gly Gly Met His Tyr Gly Val Asp Phe Phe Met Asn
            420                 425                 430
```

```
Ile Gly Thr Pro Val Lys Ala Ile Ser Ser Gly Lys Ile Val Glu Ala
        435                 440                 445
Gly Trp Ser Asn Tyr Gly Gly Asn Gln Ile Gly Leu Ile Glu Asn
    450                 455                 460
Asp Gly Val His Arg Gln Trp Tyr Met His Leu Ser Lys Tyr Asn Val
465                 470                 475                 480
Lys Val Gly Asp Tyr Val Lys Ala Gly Gln Ile Ile Gly Trp Ser Gly
                485                 490                 495
Ser Thr Gly Tyr Ser Thr Ala Pro His Leu His Phe Gln Arg Met Val
            500                 505                 510
Asn Ser Phe Ser Gln Ser Thr Ala Gln Asp Pro Met Pro Phe Leu Lys
        515                 520                 525
Ser Ala Gly Tyr Gly Lys Ala Gly Gly Thr Val Thr Pro Thr Pro Asn
        530                 535                 540
Thr Gly Trp Lys Thr Asn Lys Tyr Gly Thr Leu Tyr Lys Ser Glu Ser
545                 550                 555                 560
Ala Ser Phe Thr Pro Asn Thr Asp Ile Ile Thr Arg Thr Gly Pro
                565                 570                 575
Phe Arg Ser Met Pro Gln Ser Gly Val Leu Lys Ala Gly Gln Thr Ile
                580                 585                 590
His Tyr Asp Glu Val Met Lys Gln Asp Gly His Val Trp Val Gly Tyr
            595                 600                 605
Thr Gly Asn Ser Gly Gln Arg Ile Tyr Leu Pro Val Arg Thr Trp Gln
        610                 615                 620
Lys Ser Thr Asn Thr Leu Gly Val Leu Trp Gly Thr Ile Lys Leu Glu
625                 630                 635                 640
His His His His His His
            645

<210> SEQ ID NO 9
<211> LENGTH: 1434
<212> TYPE: DNA
<213> ORGANISM: artificial sequence
<220> FEATURE:
<223> OTHER INFORMATION: Phage K & Staphylococcus simulans

<400> SEQUENCE: 9
atggctaaga ctcaagcaga ataaataaa cgtttagatg cttatgcaaa aggaacagta      60
gatagccctt acagagttaa aaaagctaca agttatgacc catcatttgg tgtaatggaa    120
gcaggagcca ttgatgcaga tggttactat cacgctcagt gtcaagacct tattacagac    180
tatgttttat ggttaacaga taataaagtt agaacttggg gtaatgctaa agaccaaatt    240
aaacagagtt atggtactgg atttaaaata catgaaaata aaccttctac tgtacctaaa    300
aaaggttgga ttgcggtatt tacatccggt agttatgaac agtggggtca cataggtatt    360
gtatatgatg gaggtaatac ttctacattt actattttag agcaaaactg gaatggttat    420
gctaataaaa aacctacaaa acgtgtagat aattattacg gattaactca cttcattgaa    480
atacctgtaa aagcaggaac tactgttaaa aaagaaacag ctaagaaaag cgcaagtaaa    540
acgcctgcac ctaaaaagaa agcaacacta aaagtttcta agaatcacat taactataca    600
atggataaac gtggtaaaaa acctgaagga atggtaatac acaacgatgc aggtcgttct    660
tcactcgacg ctgcaacaca tgaacattca gcacaatggt tgaataatta caaaaaagga    720
tatggttacg gcccttatcc attaggtata aatggcggta tgcactacgg agttgatttt    780
tttatgaata ttgaacacc agtaaaagct atttcaagcg gaaaaatagt tgaagctggt    840
```

```
tggagtaatt acggaggagg taatcaaata ggtcttattg aaaatgatgg agtgcataga      900
caatggtata tgcatctaag taaatataat gttaaagtag gagattatgt caaagctggt      960
caaataatcg gttggtctgg aagcactggt tattctacag caccacattt acacttccaa     1020
agaatggtta actcattttc acagtcaact gcccaagatc caatgccttt cttaaagagc     1080
gcaggatatg aaaagcagg tggtacagta actccaacgc cgaatacagg ttggaaaaca      1140
aacaaatatg gcacactata taatcagag tcagctagct tcacacctaa tacagatata      1200
ataacaagaa cgactggtcc atttagaagc atgccgcagt caggagtctt aaaagcaggt     1260
caaacaattc attatgatga agtgatgaaa caagacggtc atgtttgggt aggttataca     1320
ggtaacagtg ccaacgtat ttacttgcct gtgagaacat ggcagaagtc tactaatact      1380
ctgggtgttc tgtggggaac tataaagctc gagcaccacc accaccacca ctga           1434
```

<210> SEQ ID NO 10
<211> LENGTH: 477
<212> TYPE: PRT
<213> ORGANISM: artificial sequence
<220> FEATURE:
<223> OTHER INFORMATION: Phage K & Staphylococcus simulans

<400> SEQUENCE: 10

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
    130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Leu Asp Ala
    210                 215                 220

Ala Thr His Glu His Ser Ala Gln Trp Leu Asn Asn Tyr Lys Lys Gly
225                 230                 235                 240

Tyr Gly Tyr Gly Pro Tyr Pro Leu Gly Ile Asn Gly Gly Met His Tyr
                245                 250                 255

Gly Val Asp Phe Phe Met Asn Ile Gly Thr Pro Val Lys Ala Ile Ser
```

```
                260                 265                 270
Ser Gly Lys Ile Val Glu Ala Gly Trp Ser Asn Tyr Gly Gly Asn
            275                 280                 285

Gln Ile Gly Leu Ile Glu Asn Asp Gly Val His Arg Gln Trp Tyr Met
        290                 295                 300

His Leu Ser Lys Tyr Asn Val Lys Val Gly Asp Tyr Val Lys Ala Gly
305                 310                 315                 320

Gln Ile Ile Gly Trp Ser Gly Ser Thr Gly Tyr Ser Thr Ala Pro His
                325                 330                 335

Leu His Phe Gln Arg Met Val Asn Ser Phe Ser Gln Ser Thr Ala Gln
            340                 345                 350

Asp Pro Met Pro Phe Leu Lys Ser Ala Gly Tyr Gly Lys Ala Gly Gly
        355                 360                 365

Thr Val Thr Pro Thr Pro Asn Thr Gly Trp Lys Thr Asn Lys Tyr Gly
        370                 375                 380

Thr Leu Tyr Lys Ser Glu Ser Ala Ser Phe Thr Pro Asn Thr Asp Ile
385                 390                 395                 400

Ile Thr Arg Thr Thr Gly Pro Phe Arg Ser Met Pro Gln Ser Gly Val
                405                 410                 415

Leu Lys Ala Gly Gln Thr Ile His Tyr Asp Glu Val Met Lys Gln Asp
            420                 425                 430

Gly His Val Trp Val Gly Tyr Thr Gly Asn Ser Gly Gln Arg Ile Tyr
        435                 440                 445

Leu Pro Val Arg Thr Trp Gln Lys Ser Thr Asn Thr Leu Gly Val Leu
450                 455                 460

Trp Gly Thr Ile Lys Leu Glu His His His His His His
465                 470                 475

<210> SEQ ID NO 11
<211> LENGTH: 1941
<212> TYPE: DNA
<213> ORGANISM: artificial sequence
<220> FEATURE:
<223> OTHER INFORMATION: Phage K & Staphylococcus simulans

<400> SEQUENCE: 11
atggctgcaa cacatgaaca ttcagcacaa tggttgaata attacaaaaa aggatatggt        60
tacggcccct tatccattag gtataaatgg cggtatgcact acggagttga ttttttttatg      120 aatattggaa caccagtaaa agctatttca agcggaaaaa tagttgaagc tggttggagt       180
aattacggag gaggtaatca aataggtctt attgaaaatg atggagtgca tagacaatgg       240
tatatgcatc taagtaaata taatgttaaa gtaggagatt atgtcaaagc tggtcaaata       300
atcggttggt ctggaagcac tggttattct acagcaccac atttacactt ccaaagaatg       360
gttaactcat tttcacagtc aactgcccaa gatccaatgc ctttcttaaa gagcgcagga       420
tatgaaaaag caggtggtac agtaactcca acgccgaata caggttggaa aacaaacaaa       480
tatggcacac tatataaatc agagtcagct agcttcacac taatacagaa tataataaca       540
agaacgactg gtccatttag aagcatgccg cagtcaggag tcttaaaagc aggtcaaaca       600
attcattatg atgaagtgat gaaacaagac ggtcatgttt gggtaggtta tacaggtaac       660
agtggccaac gtatttactt gcctgtgaga acatggcaga gtctactaa tactctgggt        720 gttctgtggg gaactataaa gctcgacgct aagactcaag cagaaataaa taaacgttta       780
gatgcttatg caaaaggaac agtagatagc ccttacagag ttaaaaaagc tacaagttat       840
gacccatcat ttggtgtaat ggaagcagga gccattgatg cagatggtta ctatcacgct       900
```

```
cagtgtcaag accttattac agactatgtt ttatggttaa cagataataa agttagaact    960
tggggtaatg ctaaagacca aattaaacag agttatggta ctggatttaa aatacatgaa   1020
aataaacctt ctactgtacc taaaaaaggt tggattgcgg tatttacatc cggtagttat   1080
gaacagtggg gtcacatagg tattgtatat gatggaggta atacttctac atttactatt   1140
ttagagcaaa actggaatgg ttatgctaat aaaaaaccta caaaacgtgt agataattat   1200
tacggattaa ctcacttcat tgaaatacct gtaaaagcag aactactgt taaaaaagaa    1260
acagctaaga aaagcgcaag taaaacgcct gcacctaaaa agaaagcaac actaaaagtt   1320
tctaagaatc acattaacta tacaatggat aaacgtggta aaaaacctga aggaatggta   1380
atacacaacg atgcaggtcg ttcttcagga caacaatacg agaattcatt agctaatgca   1440
ggttatgcta gatacgctaa tggtattgct cattactacg gctctgaagg ttatgtatgg   1500
gaagcaatag atgctaagaa tcaaattgct tggcacacgg gtgatggaac aggagcaaac   1560
tcaggtaact ttagatttgc aggtattgaa gtctgtcaat caatgagtgc tagtgatgct   1620
caattcctta aaaatgaaca agcagtattc caatttacag cagagaaatt taaagaatgg   1680
ggtcttactc ctaaccgtaa aactgtaaga ttgcatatgg aatttgtacc aactgcctgt   1740
cctcaccgtt ctatggttct tcatacagga tttaatccag taacacaagg aagaccatca   1800
caagcaataa tgaataaatt aaaagattat ttcattaaac aaattaaaaa ctacatggat   1860
aaaggaactt caagttctac agtagttaaa gatggtaaaa caagtagcgc aagtctcgag   1920
caccaccacc accaccactg a                                             1941
```

<210> SEQ ID NO 12
<211> LENGTH: 646
<212> TYPE: PRT
<213> ORGANISM: artificial sequence
<220> FEATURE:
<223> OTHER INFORMATION: Phage K & Staphylococcus simulans

<400> SEQUENCE: 12

```
Met Ala Ala Thr His Glu His Ser Ala Gln Trp Leu Asn Asn Tyr Lys
1               5                   10                  15

Lys Gly Tyr Gly Tyr Gly Pro Tyr Pro Leu Gly Ile Asn Gly Gly Met
            20                  25                  30

His Tyr Gly Val Asp Phe Phe Met Asn Ile Gly Thr Pro Val Lys Ala
        35                  40                  45

Ile Ser Ser Gly Lys Ile Val Glu Ala Gly Trp Ser Asn Tyr Gly Gly
    50                  55                  60

Gly Asn Gln Ile Gly Leu Ile Glu Asn Asp Gly Val His Arg Gln Trp
65                  70                  75                  80

Tyr Met His Leu Ser Lys Tyr Asn Val Lys Val Gly Asp Tyr Val Lys
                85                  90                  95

Ala Gly Gln Ile Ile Gly Trp Ser Gly Ser Thr Gly Tyr Ser Thr Ala
            100                 105                 110

Pro His Leu His Phe Gln Arg Met Val Asn Ser Phe Ser Gln Ser Thr
        115                 120                 125

Ala Gln Asp Pro Met Pro Phe Leu Lys Ser Ala Gly Tyr Gly Lys Ala
    130                 135                 140

Gly Gly Thr Val Thr Pro Thr Pro Asn Thr Gly Trp Lys Thr Asn Lys
145                 150                 155                 160

Tyr Gly Thr Leu Tyr Lys Ser Glu Ser Ala Ser Phe Thr Pro Asn Thr
                165                 170                 175
```

```
Asp Ile Ile Thr Arg Thr Thr Gly Pro Phe Arg Ser Met Pro Gln Ser
            180                 185                 190

Gly Val Leu Lys Ala Gly Gln Thr Ile His Tyr Asp Glu Val Met Lys
        195                 200                 205

Gln Asp Gly His Val Trp Val Gly Tyr Thr Gly Asn Ser Gly Gln Arg
    210                 215                 220

Ile Tyr Leu Pro Val Arg Thr Trp Gln Lys Ser Thr Asn Thr Leu Gly
225                 230                 235                 240

Val Leu Trp Gly Thr Ile Lys Leu Asp Ala Lys Thr Gln Ala Glu Ile
            245                 250                 255

Asn Lys Arg Leu Asp Ala Tyr Ala Lys Gly Thr Val Asp Ser Pro Tyr
            260                 265                 270

Arg Val Lys Lys Ala Thr Ser Tyr Asp Pro Ser Phe Gly Val Met Glu
        275                 280                 285

Ala Gly Ala Ile Asp Ala Asp Gly Tyr Tyr His Ala Gln Cys Gln Asp
    290                 295                 300

Leu Ile Thr Asp Tyr Val Leu Trp Leu Thr Asp Asn Lys Val Arg Thr
305                 310                 315                 320

Trp Gly Asn Ala Lys Asp Gln Ile Lys Gln Ser Tyr Gly Thr Gly Phe
            325                 330                 335

Lys Ile His Glu Asn Lys Pro Ser Thr Val Pro Lys Lys Gly Trp Ile
            340                 345                 350

Ala Val Phe Thr Ser Gly Ser Tyr Glu Gln Trp Gly His Ile Gly Ile
        355                 360                 365

Val Tyr Asp Gly Gly Asn Thr Ser Thr Phe Thr Ile Leu Glu Gln Asn
    370                 375                 380

Trp Asn Gly Tyr Ala Asn Lys Lys Pro Thr Lys Arg Val Asp Asn Tyr
385                 390                 395                 400

Tyr Gly Leu Thr His Phe Ile Glu Ile Pro Val Lys Ala Gly Thr Thr
            405                 410                 415

Val Lys Lys Glu Thr Ala Lys Lys Ser Ala Ser Lys Thr Pro Ala Pro
            420                 425                 430

Lys Lys Lys Ala Thr Leu Lys Val Ser Lys Asn His Ile Asn Tyr Thr
        435                 440                 445

Met Asp Lys Arg Gly Lys Lys Pro Glu Gly Met Val Ile His Asn Asp
    450                 455                 460

Ala Gly Arg Ser Ser Gly Gln Gln Tyr Glu Asn Ser Leu Ala Asn Ala
465                 470                 475                 480

Gly Tyr Ala Arg Tyr Ala Asn Gly Ile Ala His Tyr Tyr Gly Ser Glu
            485                 490                 495

Gly Tyr Val Trp Glu Ala Ile Asp Ala Lys Asn Gln Ile Ala Trp His
            500                 505                 510

Thr Gly Asp Gly Thr Gly Ala Asn Ser Gly Asn Phe Arg Phe Ala Gly
        515                 520                 525

Ile Glu Val Cys Gln Ser Met Ser Ala Ser Asp Ala Gln Phe Leu Lys
    530                 535                 540

Asn Glu Gln Ala Val Phe Gln Phe Thr Ala Glu Lys Phe Lys Glu Trp
545                 550                 555                 560

Gly Leu Thr Pro Asn Arg Lys Thr Val Arg Leu His Met Glu Phe Val
            565                 570                 575

Pro Thr Ala Cys Pro His Arg Ser Met Val Leu His Thr Gly Phe Asn
            580                 585                 590

Pro Val Thr Gln Gly Arg Pro Ser Gln Ala Ile Met Asn Lys Leu Lys
        595                 600                 605
```

Asp Tyr Phe Ile Lys Gln Ile Lys Asn Tyr Met Asp Lys Gly Thr Ser
    610                 615                 620

Ser Ser Thr Val Val Lys Asp Gly Lys Thr Ser Ser Ala Ser Leu Glu
625                 630                 635                 640

His His His His His His
            645

<210> SEQ ID NO 13
<211> LENGTH: 2214
<212> TYPE: DNA
<213> ORGANISM: artificial sequence
<220> FEATURE:
<223> OTHER INFORMATION: Phage Phi 11 & Staphylococcus simulans

<400> SEQUENCE: 13

| | |
|---|---|
| atgcaagcaa aattaactaa aaatgagttt atagagtggt tgaaaacttc tgagggaaaa | 60 |
| caattcaatg tggacttatg gtatggattt caatgctttg attatgccaa tgctggttgg | 120 |
| aaagttttgt ttggattact tctaaaaggt ttaggtgcaa agatattcc gttcgctaac | 180 |
| aacttcgacg gattagctac tgtataccaa aatacaccgg acttcttagc acaacctggc | 240 |
| gacatggtgg tattcggtag caactacggt gctggatatg gtcacgttgc atgggtaatt | 300 |
| gaagcaactt tagattacat cattgtatat gagcagaatt ggctaggcgg tggctggact | 360 |
| gacggaatcg aacaacccgg ctggggttgg aaaaagtta agacgaca catgcttat | 420 |
| gatttcccta tgtggtttat ccgtccgaat tttaaaagtg agacagcgcc acgatcagtt | 480 |
| caatctccta cacaagcacc taaaaaagaa acagctaagc acaacctaa agcagtagaa | 540 |
| cttaaaatca tcaaagatgt ggttaaaggt tatgacctac ctaagcgtgg tagtaaccct | 600 |
| aaaggtatag ttatacacaa cgacgcaggg agcaaggggg cgactgctga agcatatcgt | 660 |
| aacggattag taaatgcacc tttatcaaga ttagaagcgg gcattgcgca tagttacgta | 720 |
| tcaggcaaca cagtttggca agccttagat gaatcacaag taggttggca taccgctaat | 780 |
| caaataggta ataaatatta ttacggtatt gaagtatgtc aatcaatggg cgcagataac | 840 |
| gcgacattct aaaaaatga acaggcaact ttccaagaat cgctagatt gttgaaaaaa | 900 |
| tggggattac cagcaaacag aaatacaatc agattgcaca atgaatttac ttcaacatca | 960 |
| tgccctcata gaagttcggt tttacacact ggttttgacc cagtaactcg cggtctattg | 1020 |
| ccagaagaca gcggttgca acttaaagac tactttatca agcagattag gcgtacatg | 1080 |
| gatggtaaaa taccggttgc cactgtctct aatgagtcaa gcgcttcaag taatacagtt | 1140 |
| aaaccagttg caagtgcatg gaaacgtaat aaatatggta cttactacat ggaagaaagt | 1200 |
| gctagattca caaacggcaa tcaaccaatc acagtaagaa aagtggggcc attcttatct | 1260 |
| tgtccagtgg gttatcagtt ccaacctggt gggtattgtg attatacaga agtgatgtta | 1320 |
| caagatggtc atgtttgggt aggatataca tgggagggc aacgttatta cttgcctatt | 1380 |
| agaacatgga atggttctgc cccacctaat cagatattag gtgacttatg gggagaaatc | 1440 |
| agtctcgacg ctgcaacaca tgaacattca gcacaatggt tgaataatta caaaaaagga | 1500 |
| tatggttacg gcccttatcc attaggtata aatggcggta tgcactacgg agttgatttt | 1560 |
| tttatgaata ttgaacacc agtaaaagct atttcaagcg gaaaaatagt tgaagctggt | 1620 |
| tggagtaatt acggaggagg taatcaaata ggtcttattg aaaatgatgg agtgcataga | 1680 |
| caatggtata tgcatctaag taaatataat gttaaagtag gagattatgt caaagctggt | 1740 |
| caaataatcg gttggtctgg aagcactggt tattctacag caccacattt acacttccaa | 1800 |

-continued

```
agaatggtta actcattttc acagtcaact gcccaagatc caatgccttt cttaaagagc    1860
gcaggatatg gaaaagcagg tggtacagta actccaacgc cgaatacagg ttggaaaaca    1920
aacaaatatg gcacactata taaatcagag tcagctagct tcacacctaa tacagatata    1980
ataacaagaa cgactggtcc atttagaagc atgccgcagt caggagtctt aaaagcaggt    2040
caaacaattc attatgatga agtgatgaaa caagacggtc atgtttgggt aggttataca    2100
ggtaacagtg ccaacgtat ttacttgcct gtgagaacat ggcagaagtc tactaatact    2160
ctgggtgttc tgtggggaac tataaagctc gagcaccacc accaccacca ctga          2214
```

<210> SEQ ID NO 14
<211> LENGTH: 737
<212> TYPE: PRT
<213> ORGANISM: artificial sequence
<220> FEATURE:
<223> OTHER INFORMATION: Phage Phi 11 & Staphylococcus simulans

<400> SEQUENCE: 14

```
Met Gln Ala Lys Leu Thr Lys Asn Glu Phe Ile Glu Trp Leu Lys Thr
1               5                   10                  15

Ser Glu Gly Lys Gln Phe Asn Val Asp Leu Trp Tyr Gly Phe Gln Cys
            20                  25                  30

Phe Asp Tyr Ala Asn Ala Gly Trp Lys Val Leu Phe Gly Leu Leu Leu
        35                  40                  45

Lys Gly Leu Gly Ala Lys Asp Ile Pro Phe Ala Asn Asn Phe Asp Gly
    50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
            100                 105                 110

Asn Trp Leu Gly Gly Gly Trp Thr Asp Gly Ile Glu Gln Pro Gly Trp
        115                 120                 125

Gly Trp Glu Lys Val Thr Arg Arg Gln His Ala Tyr Asp Phe Pro Met
    130                 135                 140

Trp Phe Ile Arg Pro Asn Phe Lys Ser Glu Thr Ala Pro Arg Ser Val
145                 150                 155                 160

Gln Ser Pro Thr Gln Ala Pro Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Ser Asn Pro Lys Gly Ile Val Ile His Asn Asp
        195                 200                 205

Ala Gly Ser Lys Gly Ala Thr Ala Glu Ala Tyr Arg Asn Gly Leu Val
    210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Tyr Tyr Gly Ile Glu Val
            260                 265                 270

Cys Gln Ser Met Gly Ala Asp Asn Ala Thr Phe Leu Lys Asn Glu Gln
        275                 280                 285

Ala Thr Phe Gln Glu Cys Ala Arg Leu Leu Lys Lys Trp Gly Leu Pro
    290                 295                 300
```

```
Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
            325                 330                 335

Arg Gly Leu Leu Pro Glu Asp Lys Arg Leu Gln Leu Lys Asp Tyr Phe
        340                 345                 350

Ile Lys Gln Ile Arg Ala Tyr Met Asp Gly Lys Ile Pro Val Ala Thr
    355                 360                 365

Val Ser Asn Glu Ser Ser Ala Ser Ser Asn Thr Val Lys Pro Val Ala
370                 375                 380

Ser Ala Trp Lys Arg Asn Lys Tyr Gly Thr Tyr Tyr Met Glu Glu Ser
385                 390                 395                 400

Ala Arg Phe Thr Asn Gly Asn Gln Pro Ile Thr Val Arg Lys Val Gly
                405                 410                 415

Pro Phe Leu Ser Cys Pro Val Gly Tyr Gln Phe Gln Pro Gly Gly Tyr
            420                 425                 430

Cys Asp Tyr Thr Glu Val Met Leu Gln Asp Gly His Val Trp Val Gly
            435                 440                 445

Tyr Thr Trp Glu Gly Gln Arg Tyr Tyr Leu Pro Ile Arg Thr Trp Asn
    450                 455                 460

Gly Ser Ala Pro Pro Asn Gln Ile Leu Gly Asp Leu Trp Gly Glu Ile
465                 470                 475                 480

Ser Leu Asp Ala Ala Thr His Glu His Ser Ala Gln Trp Leu Asn Asn
            485                 490                 495

Tyr Lys Lys Gly Tyr Gly Tyr Gly Pro Tyr Pro Leu Gly Ile Asn Gly
            500                 505                 510

Gly Met His Tyr Gly Val Asp Phe Phe Met Asn Ile Gly Thr Pro Val
        515                 520                 525

Lys Ala Ile Ser Ser Gly Lys Ile Val Glu Ala Gly Trp Ser Asn Tyr
    530                 535                 540

Gly Gly Gly Asn Gln Ile Gly Leu Ile Glu Asn Asp Gly Val His Arg
545                 550                 555                 560

Gln Trp Tyr Met His Leu Ser Lys Tyr Asn Val Lys Val Gly Asp Tyr
                565                 570                 575

Val Lys Ala Gly Gln Ile Ile Gly Trp Ser Gly Ser Thr Gly Tyr Ser
            580                 585                 590

Thr Ala Pro His Leu His Phe Gln Arg Met Val Asn Ser Phe Ser Gln
    595                 600                 605

Ser Thr Ala Gln Asp Pro Met Pro Phe Leu Lys Ser Ala Gly Tyr Gly
610                 615                 620

Lys Ala Gly Gly Thr Val Thr Pro Thr Pro Asn Thr Gly Trp Lys Thr
625                 630                 635                 640

Asn Lys Tyr Gly Thr Leu Tyr Lys Ser Glu Ser Ala Ser Phe Thr Pro
                645                 650                 655

Asn Thr Asp Ile Ile Thr Arg Thr Thr Gly Pro Phe Arg Ser Met Pro
            660                 665                 670

Gln Ser Gly Val Leu Lys Ala Gly Gln Thr Ile His Tyr Asp Glu Val
        675                 680                 685

Met Lys Gln Asp Gly His Val Trp Val Gly Tyr Thr Gly Asn Ser Gly
        690                 695                 700

Gln Arg Ile Tyr Leu Pro Val Arg Thr Trp Gln Lys Ser Thr Asn Thr
705                 710                 715                 720

Leu Gly Val Leu Trp Gly Thr Ile Lys Leu Glu His His His His His
```

His

<210> SEQ ID NO 15
<211> LENGTH: 1470
<212> TYPE: DNA
<213> ORGANISM: artificial sequence
<220> FEATURE:
<223> OTHER INFORMATION: Phi 11

<400> SEQUENCE: 15

```
atgcaagcaa aattaactaa aaatgagttt atagagtggt tgaaaacttc tgagggaaaa      60
caattcaatg tggacttatg gtatggattt caatgctttg attatgccaa tgctggttgg     120
aaagttttgt ttggattact tctaaaaggt ttaggtgcaa agatattcc gttcgctaac      180
aacttcgacg gattagctac tgtataccaa aatacaccgg acttcttagc acaacctggc     240
gacatggtgg tattcggtag caactacggt gctggatatg gtcacgttgc atgggtaatt     300
gaagcaactt tagattacat cattgtatat gagcagaatt ggctaggcgg tggctggact     360
gacggaatcg aacaacccgg ctggggttgg gaaaaagtta caagacgaca acatgcttat     420
gatttcccta tgtggtttat ccgtccgaat tttaaaagtg agacagcgcc acgatcagtt     480
caatctccta cacaagcacc taaaaaagaa acagctaagc cacaacctaa agcagtagaa     540
cttaaaatca tcaaagatgt ggttaaaggt tatgacctac ctaagcgtgg tagtaaccct     600
aaaggtatag ttatacacaa cgacgcaggg agcaaagggg cgactgctga agcatatcgt     660
aacggattag taaatgcacc tttatcaaga ttagaagcgg gcattgcgca tagttacgta     720
tcaggcaaca cagtttggca agccttagat gaatcacaag taggttggca taccgctaat     780
caaataggta ataaatatta ttacggtatt gaagtatgtc aatcaatggg cgcagataac     840
gcgacattct aaaaaatga acaggcaact ttccaagaat gcgctagatt gttgaaaaaa     900
tggggattac cagcaaacag aaatacaatc agattgcaca atgaatttac ttcaacatca     960
tgccctcata gaagttcggt tttacacact ggttttgacc cagtaactcg cggtctattg    1020
ccagaagaca agcggttgca acttaaagac tactttatca agcagattag ggcgtacatg    1080
gatggtaaaa taccggttgc cactgtctct aatgagtcaa gcgcttcaag taatacagtt    1140
aaaccagttg caagtgcatg gaaacgtaat aaatatggta cttactacat ggaagaaagt    1200
gctagattca aaacggcaa tcaaccaatc acagtaagaa agtggggcc attcttatct    1260
tgtccagtgg gttatcagtt ccaacctggt gggtattgtg attatacaga gtgatgttaa   1320
caagatggtc atgtttgggt aggatataca tgggaggggc aacgttatta cttgcctatt    1380
agaacatgga atggttctgc cccacctaat cagatattag gtgacttatg gggagaaatc    1440
agtctcgagc accaccacca ccaccactga                                     1470
```

<210> SEQ ID NO 16
<211> LENGTH: 489
<212> TYPE: PRT
<213> ORGANISM: artificial sequence
<220> FEATURE:
<223> OTHER INFORMATION: Phi 11

<400> SEQUENCE: 16

Met Gln Ala Lys Leu Thr Lys Asn Glu Phe Ile Glu Trp Leu Lys Thr
1               5                   10                  15

Ser Glu Gly Lys Gln Phe Asn Val Asp Leu Trp Tyr Gly Phe Gln Cys
            20                  25                  30

-continued

Phe Asp Tyr Ala Asn Ala Gly Trp Lys Val Leu Phe Gly Leu Leu Leu
            35                  40                  45

Lys Gly Leu Gly Ala Lys Asp Ile Pro Phe Ala Asn Asn Phe Asp Gly
 50                  55                  60

Leu Ala Thr Val Tyr Gln Asn Thr Pro Asp Phe Leu Ala Gln Pro Gly
 65                  70                  75                  80

Asp Met Val Val Phe Gly Ser Asn Tyr Gly Ala Gly Tyr Gly His Val
                 85                  90                  95

Ala Trp Val Ile Glu Ala Thr Leu Asp Tyr Ile Ile Val Tyr Gln Gln
            100                 105                 110

Asn Trp Leu Gly Gly Trp Thr Asp Gly Ile Glu Gln Pro Gly Trp
            115                 120                 125

Gly Trp Glu Lys Val Thr Arg Arg Gln His Ala Tyr Asp Phe Pro Met
130                 135                 140

Trp Phe Ile Arg Pro Asn Phe Lys Ser Glu Thr Ala Pro Arg Ser Val
145                 150                 155                 160

Gln Ser Pro Thr Gln Ala Pro Lys Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Ser Asn Pro Lys Gly Ile Val Ile His Asn Asp
            195                 200                 205

Ala Gly Ser Lys Gly Ala Thr Ala Glu Ala Tyr Arg Asn Gly Leu Val
210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255

His Thr Ala Asn Gln Ile Gly Asn Lys Tyr Tyr Tyr Gly Ile Glu Val
            260                 265                 270

Cys Gln Ser Met Gly Ala Asp Asn Ala Thr Phe Leu Lys Asn Glu Gln
            275                 280                 285

Ala Thr Phe Gln Glu Cys Ala Arg Leu Leu Lys Lys Trp Gly Leu Pro
290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Arg Leu Gln Leu Lys Asp Tyr Phe
            340                 345                 350

Ile Lys Gln Ile Arg Ala Tyr Met Asp Gly Lys Ile Pro Val Ala Thr
            355                 360                 365

Val Ser Asn Glu Ser Ser Ala Ser Ser Asn Thr Val Lys Pro Val Ala
370                 375                 380

Ser Ala Trp Lys Arg Asn Lys Tyr Gly Thr Tyr Tyr Met Glu Glu Ser
385                 390                 395                 400

Ala Arg Phe Thr Asn Gly Asn Gln Pro Ile Thr Val Arg Lys Val Gly
                405                 410                 415

Pro Phe Leu Ser Cys Pro Val Gly Tyr Gln Phe Gln Pro Gly Gly Tyr
            420                 425                 430

Cys Asp Tyr Thr Glu Val Met Leu Gln Asp Gly His Val Trp Val Gly
            435                 440                 445

Tyr Thr Trp Glu Gly Gln Arg Tyr Tyr Leu Pro Ile Arg Thr Trp Asn
450                 455                 460

Gly Ser Ala Pro Pro Asn Gln Ile Leu Gly Asp Leu Trp Gly Glu Ile
465                 470                 475                 480

Ser Leu Glu His His His His His His
            485

<210> SEQ ID NO 17
<211> LENGTH: 25
<212> TYPE: DNA
<213> ORGANISM: artificial sequence
<220> FEATURE:
<223> OTHER INFORMATION: Chemically Synthesized

<400> SEQUENCE: 17
gagaaattac atatggctaa gactc                                            25

<210> SEQ ID NO 18
<211> LENGTH: 27
<212> TYPE: DNA
<213> ORGANISM: artificial sequence
<220> FEATURE:
<223> OTHER INFORMATION: Chemically Synthesized

<400> SEQUENCE: 18
atggtgatgc tcgagtttga atactcc                                          27

<210> SEQ ID NO 19
<211> LENGTH: 39
<212> TYPE: DNA
<213> ORGANISM: artificial sequence
<220> FEATURE:
<223> OTHER INFORMATION: Chemically Synthesized

<400> SEQUENCE: 19
acgtacgtca tatggctgca acacatgaac attcagcac                             39

<210> SEQ ID NO 20
<211> LENGTH: 32
<212> TYPE: DNA
<213> ORGANISM: artificial sequence
<220> FEATURE:
<223> OTHER INFORMATION: Chemically Synthesized

<400> SEQUENCE: 20
gcgctactcg agaccacctg cttttccata tc                                    32

<210> SEQ ID NO 21
<211> LENGTH: 37
<212> TYPE: DNA
<213> ORGANISM: artificial sequence
<220> FEATURE:
<223> OTHER INFORMATION: Chemically Synthesized

<400> SEQUENCE: 21
atcatcgtcg acgctgcaac acatgaacat tcagcac                               37

<210> SEQ ID NO 22
<211> LENGTH: 33
<212> TYPE: DNA
<213> ORGANISM: artificial sequence
<220> FEATURE:
<223> OTHER INFORMATION: Chemically Synthesized

<400> SEQUENCE: 22
gtggtgctcg agacttgcgc tacttgtttt acc                                   33

```
<210> SEQ ID NO 23
<211> LENGTH: 20
<212> TYPE: DNA
<213> ORGANISM: artificial sequence
<220> FEATURE:
<223> OTHER INFORMATION: Chemically Synthesized

<400> SEQUENCE: 23
ggataacaat tccctctag                                                   20

<210> SEQ ID NO 24
<211> LENGTH: 27
<212> TYPE: DNA
<213> ORGANISM: artificial sequence
<220> FEATURE:
<223> OTHER INFORMATION: Chemically Synthesized

<400> SEQUENCE: 24
gtattgctcg agtgaagaac gacctgc                                          27

<210> SEQ ID NO 25
<211> LENGTH: 22
<212> TYPE: DNA
<213> ORGANISM: artificial sequence
<220> FEATURE:
<223> OTHER INFORMATION: Chemically Synthesized

<400> SEQUENCE: 25
gatatagtcg acgctaagac tc                                               22

<210> SEQ ID NO 26
<211> LENGTH: 25
<212> TYPE: DNA
<213> ORGANISM: artificial sequence
<220> FEATURE:
<223> OTHER INFORMATION: Chemically Synthesized

<400> SEQUENCE: 26
cgtttagagg ccccaagggg ttatg                                            25

<210> SEQ ID NO 27
<211> LENGTH: 26
<212> TYPE: DNA
<213> ORGANISM: artificial sequence
<220> FEATURE:
<223> OTHER INFORMATION: Chemically Synthesized

<400> SEQUENCE: 27
gtggcgcata tgcaagcaaa attaac                                           26

<210> SEQ ID NO 28
<211> LENGTH: 25
<212> TYPE: DNA
<213> ORGANISM: artificial sequence
<220> FEATURE:
<223> OTHER INFORMATION: Chemically Synthesized

<400> SEQUENCE: 28
tgactatgtc ctcgagactg atttc                                            25

<210> SEQ ID NO 29
<211> LENGTH: 1974
<212> TYPE: DNA
<213> ORGANISM: artificial sequence
<220> FEATURE:
<223> OTHER INFORMATION: Staphylococcus simulans & Phage K

<400> SEQUENCE: 29
```

```
atggctgcaa cacatgaaca ttcagcacaa tggttgaata attacaaaaa aggatatggt      60 tacggcccett atccattagg tataaatggc ggtatgcact acggagttga ttttttatg     120 aatattggaa caccagtaaa agctatttca agcggaaaaa tagttgaagc tggttggagt     180
aattacggag gaggtaatca aataggtctt attgaaaatg atggagtgca tagacaatgg     240
tatatgcatc taagtaaata taatgttaaa gtaggagatt atgtcaaagc tggtcaaata     300
atcggttggt ctggaagcac tggttattct acagcaccac atttacactt ccaaagaatg     360
gttaattcat tttcaaattc aactgcccaa gatccaatgc ctttcttaaa gagcgcagga     420 tatgaaaag caggtggtac agtaactcca acgccgaata caggtctcga cgctaagact     480
caagcagaaa taaataaacg tttagatgct tatgcaaaag aacagtagaa tagcccttac     540
agagttaaaa aagctacaag ttatgaccca tcatttggtg taatggaagc aggagccatt     600
gatgcagatg gttactatca cgctcagtgt caagaccta ttacagacta tgttttatgg     660
ttaacagata ataaagttag aacttggggt aatgctaaag accaaattaa acagagttat     720
ggtactggat ttaaaataca tgaaaataaa ccttctactg tacctaaaaa aggttggatt     780
gcggtattta catccggtag ttatgaacag tggggtcaca taggtattgt atatgatgga     840
ggtaatactt ctacatttac tattttagag caaaactgga atggttatgc taataaaaaa     900
cctacaaaac gtgtagataa ttattacgga ttaactcact tcattgaaat acctgtaaaa     960
gcaggaacta ctgttaaaaa agaaacagct aagaaaagcg caagtaaaac gcctgcacct    1020
aaaaagaaag caacactaaa agtttctaag aatcacatta actatacaat ggataaacgt    1080
ggtaaaaaac ctgaaggaat ggtaatacac aacgatgcag gtcgttcttc aggacaacaa    1140
tacgagaatt cattagctaa tgcaggttat gctagatacg ctaatggtat tgctcattac    1200
tacggctctg aaggttatgt atgggaagca atagatgcta agaatcaaat tgcttggcac    1260
acgggtgatg gaacaggagc aaaactcggg aactttagat ttgcaggtat tgaagtctgt    1320
caatcaatga gtgctagtga tgctcaattc cttaaaaatg aacaagcagt attccaattt    1380
acagcagaga aatttaaaga atggggtctt actcctaacc gtaaaactgt aagattgcat    1440
atggaatttg taccaactgc ctgtcctcac cgttctatgg ttcttcatac aggatttaat    1500
ccagtaacac aaggaagacc atcacaagca ataatgaata aattaaaaga ttatttcatt    1560
aaacaaatta aaaactacat ggataaagga acttcgagtt ctacagtagt taaagatggt    1620
aaaacaagta gcgcaagtct cgacacagta actccaacgc cgaatacagg ttggaaaaca    1680
aacaaatatg gcacactata taaatcagag tcagctagct tcacacctaa tacagatata    1740
ataacaagaa cgactggtcc atttagaagc atgccgcagt caggagtctt aaaagcaggt    1800
caaacaattc attatgatga agtgatgaaa caagacggtc atgtttgggt aggttataca    1860
ggtaacagtg gccaacgtat ttacttgcct gtaagaacat ggaataagtc tactaatact    1920
ctgggtgttc tgtggggaac tataaagctc gagcaccacc accaccacca ctga          1974
```

<210> SEQ ID NO 30
<211> LENGTH: 657
<212> TYPE: PRT
<213> ORGANISM: artificial sequence
<220> FEATURE:
<223> OTHER INFORMATION: Staphylococcus simulans & Phage K

<400> SEQUENCE: 30

```
Met Ala Ala Thr His Glu His Ser Ala Gln Trp Leu Asn Asn Tyr Lys
1               5                   10                  15
```

-continued

Lys Gly Tyr Gly Tyr Gly Pro Tyr Pro Leu Gly Ile Asn Gly Gly Met
            20              25              30

His Tyr Gly Val Asp Phe Phe Met Asn Ile Gly Thr Pro Val Lys Ala
        35              40              45

Ile Ser Ser Gly Lys Ile Val Glu Ala Gly Trp Ser Asn Tyr Gly Gly
50              55              60

Gly Asn Gln Ile Gly Leu Ile Glu Asn Asp Gly Val His Arg Gln Trp
65              70              75              80

Tyr Met His Leu Ser Lys Tyr Asn Val Lys Val Gly Asp Tyr Val Lys
                85              90              95

Ala Gly Gln Ile Ile Gly Trp Ser Gly Ser Thr Gly Tyr Ser Thr Ala
            100             105             110

Pro His Leu His Phe Gln Arg Met Val Asn Ser Phe Ser Asn Ser Thr
        115             120             125

Ala Gln Asp Pro Met Pro Phe Leu Lys Ser Ala Gly Tyr Gly Lys Ala
130             135             140

Gly Gly Thr Val Thr Pro Thr Pro Asn Thr Gly Leu Asp Ala Lys Thr
145             150             155             160

Gln Ala Glu Ile Asn Lys Arg Leu Asp Ala Tyr Ala Lys Gly Thr Val
                165             170             175

Asp Ser Pro Tyr Arg Val Lys Lys Ala Thr Ser Tyr Asp Pro Ser Phe
            180             185             190

Gly Val Met Glu Ala Gly Ala Ile Asp Ala Asp Gly Tyr Tyr His Ala
        195             200             205

Gln Cys Gln Asp Leu Ile Thr Asp Tyr Val Leu Trp Leu Thr Asp Asn
210             215             220

Lys Val Arg Thr Trp Gly Asn Ala Lys Asp Gln Ile Lys Gln Ser Tyr
225             230             235             240

Gly Thr Gly Phe Lys Ile His Glu Asn Lys Pro Ser Thr Val Pro Lys
                245             250             255

Lys Gly Trp Ile Ala Val Phe Thr Ser Gly Ser Tyr Glu Gln Trp Gly
            260             265             270

His Ile Gly Ile Val Tyr Asp Gly Gly Asn Thr Ser Thr Phe Thr Ile
        275             280             285

Leu Glu Gln Asn Trp Asn Gly Tyr Ala Asn Lys Lys Pro Thr Lys Arg
290             295             300

Val Asp Asn Tyr Tyr Gly Leu Thr His Phe Ile Glu Ile Pro Val Lys
305             310             315             320

Ala Gly Thr Thr Val Lys Lys Glu Thr Ala Lys Lys Ser Ala Ser Lys
                325             330             335

Thr Pro Ala Pro Lys Lys Lys Ala Thr Leu Lys Val Ser Lys Asn His
            340             345             350

Ile Asn Tyr Thr Met Asp Lys Arg Gly Lys Lys Pro Glu Gly Met Val
        355             360             365

Ile His Asn Asp Ala Gly Arg Ser Gly Gln Gln Tyr Glu Asn Ser
370             375             380

Leu Ala Asn Ala Gly Tyr Ala Arg Tyr Ala Asn Gly Ile Ala His Tyr
385             390             395             400

Tyr Gly Ser Glu Gly Tyr Val Trp Glu Ala Ile Asp Ala Lys Asn Gln
                405             410             415

Ile Ala Trp His Thr Gly Asp Gly Thr Gly Ala Asn Ser Gly Asn Phe
            420             425             430

Arg Phe Ala Gly Ile Glu Val Cys Gln Ser Met Ser Ala Ser Asp Ala
        435             440             445

```
Gln Phe Leu Lys Asn Glu Gln Ala Val Phe Gln Phe Thr Ala Glu Lys
    450                 455                 460

Phe Lys Glu Trp Gly Leu Thr Pro Asn Arg Lys Thr Val Arg Leu His
465                 470                 475                 480

Met Glu Phe Val Pro Thr Ala Cys Pro His Arg Ser Met Val Leu His
                485                 490                 495

Thr Gly Phe Asn Pro Val Thr Gln Gly Arg Pro Ser Gln Ala Ile Met
                500                 505                 510

Asn Lys Leu Lys Asp Tyr Phe Ile Lys Gln Ile Lys Asn Tyr Met Asp
            515                 520                 525

Lys Gly Thr Ser Ser Thr Val Val Lys Asp Gly Lys Thr Ser Ser
    530                 535                 540

Ala Ser Leu Asp Thr Val Thr Pro Thr Asn Thr Gly Trp Lys Thr
545                 550                 555                 560

Asn Lys Tyr Gly Thr Leu Tyr Lys Ser Glu Ser Ala Ser Phe Thr Pro
                565                 570                 575

Asn Thr Asp Ile Ile Thr Arg Thr Thr Gly Pro Phe Arg Ser Met Pro
                580                 585                 590

Gln Ser Gly Val Leu Lys Ala Gly Gln Thr Ile His Tyr Asp Glu Val
            595                 600                 605

Met Lys Gln Asp Gly His Val Trp Val Gly Tyr Thr Gly Asn Ser Gly
610                 615                 620

Gln Arg Ile Tyr Leu Pro Val Arg Thr Trp Asn Lys Ser Thr Asn Thr
625                 630                 635                 640

Leu Gly Val Leu Trp Gly Thr Ile Lys Leu Glu His His His His His
                645                 650                 655

His

<210> SEQ ID NO 31
<211> LENGTH: 24
<212> TYPE: DNA
<213> ORGANISM: artificial sequence
<220> FEATURE:
<223> OTHER INFORMATION: Chemically Synthesized

<400> SEQUENCE: 31
gtttgtctcg agacctgtat tcgg                                         24

<210> SEQ ID NO 32
<211> LENGTH: 30
<212> TYPE: DNA
<213> ORGANISM: artificial sequence
<220> FEATURE:
<223> OTHER INFORMATION: Chemically Synthesized

<400> SEQUENCE: 32
gcgcatctcg agacagtaac tccaacgccg                                   30

<210> SEQ ID NO 33
<211> LENGTH: 4
<212> TYPE: PRT
<213> ORGANISM: Staphylococcus aureus

<400> SEQUENCE: 33

Ala Gln Lys Ala
1

<210> SEQ ID NO 34
<211> LENGTH: 5
```

```
<212> TYPE: PRT
<213> ORGANISM: Staphylococcus aureus

<400> SEQUENCE: 34

Gly Gly Gly Gly Gly
1               5

<210> SEQ ID NO 35
<211> LENGTH: 5
<212> TYPE: PRT
<213> ORGANISM: Staphylococcus aureus

<400> SEQUENCE: 35

Ala Gln Lys Ala Gly
1               5
```

TRIPLE ACTING ANTIMICROBIALS THAT ARE REFRACTORY TO RESISTANCE DEVELOPMENT

This application claims the benefit of U.S. Provisional Application No. 61/35,810, filed Jul. 24, 2008, which is incorporated herein by reference in its entirety.

BACKGROUND OF THE INVENTION

1. Field of the Invention

This invention relates to constructs comprising three antimicrobial domains each harboring a unique lytic activity: a CHAP endopeptidase, an amidase, and a glycyl-glycine endopeptidase. In one embodiment, the CHAP endopeptidase and the amidase are provided by the peptidoglycan hydrolase, LysK endolysin, and the glycyl-glycine endopeptidase is provided by another peptidoglycan hydrolase, Lysostaphin generating a pathogen-specific triple fusion construct. The LysK endolysin specifically attacks the peptidoglycan cell wall of untreated, live staphylococci including *S. aureus* and methicillin-resistant *Staphylococcus aureus* (MRSA); Lysostaphin is a potent anti-staphylococcal bacteriocin. The constructs comprising the three functional antimicrobial domains are designed to be refractory to resistance development and can be used to treat staphylococcal pathogens including multi-drug resistant strains MRSA and USA300.

2. Description of the Relevant Art

*S. aureus* is an opportunistic bacterial pathogen responsible for a diverse spectrum of human and animal diseases. Although *S. aureus* may colonize mucosal surfaces of healthy humans, it is also a major cause of wound infections and has the invasive potential to induce severe infections, including osteomyelitis, endocarditis, and bacteremia with metastatic complications (Lowy, F. D. 1998. *New England J. Med.* 339: 520-532). Coagulase-negative staphylococci (CoNS) and *S. aureus* are the most common pathogens in nosocomial bacteremias and infections of implanted devices (Gordon et al. 2001. *Ann. Thorac. Surg.* 72: 725-730; Malani et al. 2002. *Clin. Infect. Dis.* 34: 1295-1300. Although methicillin-resistant *S. aureus* (MRSA) has classically been regarded as a nosocomial pathogen, it has emerged as a cause of community-acquired infections in hosts without predisposing risk factors. Superficial skin and soft tissue infections caused by MRSA are increasingly seen in clinical practice. There are limited treatment options available in terms of topical antimicrobial agents, and some strains of MRSA have developed resistance to topically applied antimicrobial agents. MRSA account for 40%-60% of nosocomial *S. aureus* infections in the U.S., and many of these strains are multi-drug resistant. Recent data indicate that more patients in U.S. hospitals die from MRSA (>18,000 per year) than AIDS (Klevens et al. 2007. *JAMA* 298: 1763-1771). MRSA strains with reduced susceptibility or resistance to vancomycin have also been reported (Zhu et al. 2008. *Antimicrob. Agents Chemother.* 52: 452-457). Because *S. aureus* cannot always be controlled by antibiotics and because MRSA isolates are becoming increasingly prevalent in the community, additional control strategies are sorely needed.

Peptidoglycan is the major structural component of the bacterial cell wall and can be up to 40 layers thick. Bacteria have autolytic peptidoglycan hydrolases that allow the cell to grow and divide. Another well-studied group of peptidoglycan hydrolase enzymes are the bacteriophage (viruses that infect bacteria) endolysins. Endolysins allow the phage to escape from the bacterial cell during the phage lytic cycle. Some Gram-positive bacteria exposed to purified phage lysins externally undergo exolysis or "lysis from without." Use of phage endolysins as antimicrobials has not been reported for treatment of Gram-negative bacteria, presumably due to the presence of an outer membrane that prevents access to the peptidoglycan (Loessner, M. J. 2005. *Curr. Opin. Microbiol.* 8: 480-487). Peptidoglycan is unique to bacteria and has a complex structure (Loessner, supra) with a sugar backbone of alternating units of N-acetyl glucosamine (GN) and N-acetylmuramic acid (MN). Each MN residue is amide linked to a short pentapeptide chain. Characteristic of *S. aureus* is the pentaglycine bridge that connects the L-Lys of the stem peptide to the D-Ala at position 4 of a neighboring subunit (FIG. 1). Peptidoglycan hydrolases have evolved a modular design to deal with this complexity. Although single domain endolysins can lyse the target pathogen (Sanz et al. 1996. *Eur. J. Biochem.* 235: 601-605), endolysins can also harbor two short domains (~100-200 amino acids), each encoding a different peptidoglycan hydrolase activity.

Three classes of peptidoglycan hydrolase domains have been identified: endopeptidases, amidases, and glycosidases (includes glucosaminidase and lysozyme-like muramidases) (Lopez and Garcia. 2004. *FEMS Microbiol. Rev.* 28: 553-580; FIG. 1). Alignment of conserved domain sequences from multiple peptidoglycan hydrolase proteins has identified non-variant amino acid positions that, when mutated, can destroy the hydrolytic activity of the domain (Pritchard et al. 2004. *Microbiology* 150: 2079-2087; Huard et al. 2003. *Microbiology* 149: 695-705; Bateman and Rawlings. 2003. *Trends Biochem. Sci.* 28: 234-237; Rigden et al. 2003. *Trends Biochem. Sci.* 28: 230-234). Chimeric peptidoglycan hydrolases have been created by the exchange of cell wall binding domains of two lysins (Croux et al. 1993. *Mol. Microbiol.* 9: 1019-1025). Enzymatic activity was retained and regulatory properties exchanged when the cell wall binding domains of choline-binding pneumococcal and clostridial lysins were swapped. Intra-generic chimeric fusion lysins are also functional (Diaz et al. 1990. *Proc. Natl. Acad. Sci. USA* 87: 8125-8129).

Lysostaphin is a bacteriocin secreted by *S. simulans*, that lyses *S. aureus* (Browder et al. 1965. *Biochem. Biophys. Res. Commun.* 19: 389). The endopeptidase activity is specific to the glycyl-glycyl bonds of the staphylococcal peptidoglycan inter-peptide bridge (FIG. 1). It is known that Lysostaphin can kill planktonic *S. aureus* (Walencka et al. 2005. *Pol. J. Microbiol.* 54: 191-200; Wu et al. 2003. *Antimicrob. Agents Chemother.* 47: 3407-3414), as well as MRSA (Dajcs et al. 2000. *Am. J. Opthalmol.* 130: 544), vancomycin-intermediate *S. aureus* (Patron et al. 1999. *Antimicrob. Agents Chemother.* 43:1754-1755), and other antibiotic-resistant strains of *S. aureus* (Peterson et al. 1978. *J. Clin. Invest.* 61: 597-609). Lysostaphin can also kill *S. aureus* growing in a biofilm (Walencka, supra; Wu, supra), and it exhibits limited activity against CoNS (Cisani et al. 1982. *Antimicrob. Agents Chemother.* 21: 531-535); McCormick et al. 2006. *Curr. Eye Res.* 31: 225-230).

*S. simulans* produces Lysostaphin and avoids its lytic action by the product of the Lysostaphin immunity factor (lif) gene [same as endopeptidase resistance gene (epr) (DeHart et al. 1995. *Appl. Environ. Microbiol.* 61: 1475-1479) that resides on a native plasmid (pACK1) (Thumm and Gotz. 1997. *Mol. Microbiol.* 23: 1251-1265). The lif gene product functions by inserting serine residues into the peptidoglycan cross bridge, thus interfering with the ability of the glycyl-glycyl endopeptidase to recognize and cleave this structure. Similarly, mutations in the *S. aureus* femA gene (factor essential for methicillin resistance) (Sugai et al., 1997. *J. Bacteriol.* 179: 4311-4318) result in a reduction in the peptidoglycan interpeptide cross bridge from pentaglycine to a single glycine, rendering S. aureus resistant to the lytic action of Lysostaphin. MRSA have been shown to mutate femA when exposed in vitro or in vivo to sub-inhibitory doses of Lysostaphin (Climo et al. 2001. *Antimicrob. Agents Chemother.* 45: 1431-1437).

Grundling et al. identified lyrA (Lysostaphin resistance A) that, when mutated by a transposon insertion, reduced *S. aureus* susceptibility to Lysostaphin (Grundling et al. 2006. *J. Bacteriol.* 188: 6286-6297). Although some structural changes were noted in peptidoglycan purified from the mutant, the purified peptidoglycan was susceptible to Lysostaphin and the phi11 endolysin, suggesting that changes in accessibility of the enzyme to its substrate may have rendered the strain Lysostaphin resistant.

Bacterial resistance to antibiotics usually involves the acquisition of enzymes that 1) inactivate the antibiotic; 2) reduce membrane permeability; 3) facilitate active efflux of the antimicrobial from the cell; 4) modify the target protein to a resistant form; or 5) produce higher quantities of the target protein. Alternatively, the original target protein can be 6) altered via a mutational or recombination event at the endogenous gene to an antibiotic-resistant form; or 7) the organism can be protected through the multi-faceted changes that accompany growth in a biofilm (Spratt, B. G. 1994. *Science* 264: 388-393).

The Gram-positive peptidoglycan is on the cell surface, outside of the cell membrane. Many mechanisms of resistance development take advantage of the ability to inactivate the antimicrobial inside the cell. Targets outside the cytoplasmic membrane reduce the possible mechanisms by which resistance can emerge (Spratt, supra). Although there have been no reports of extracellular inactivation of peptidoglycan hydrolase enzymes, *S. aureus* does secrete proteases that might degrade peptidoglycan hydrolases. A regulatory mutation that increases the activity, synthesis, regulation, or secretion of staphylococcal proteases (such as sarA (Karlsson et al. 2001. *Infect. Immun.* 69: 4742-4748) might confer some level of resistance. Similarly, although phi11 and Lysostaphin could digest purified lyrA peptidoglycan, this mutant is slightly resistant to Lysostaphin, suggesting that resistance mechanisms could exist due to changes in surface structures that limit accessibility to the target peptidoglycan (Grundling, supra). O-acetylation of peptidoglycan N-acetyl muramic acid residues by an O-acetyltransferase (OatA) results in resistance to human lysozyme and correlates with heightened virulence of some *S. aureus* strains (Bera et al. 2006. *Infect. Immun.* 74: 4598-4604).

Bacteriophage endolysins are relatively new antimicrobials compared to Lysostaphin, which was described in the 1960's (Browder, supra). Despite repeated attempts, no strains of bacteria that can resist lysis by bacteriophage endolysins have been reported (Loeffler et al. 2001. *Science* 294: 2170-2172: Schuch et al. 2002. *Nature* 418: 884-889; Fischetti, V. A. 2005. *Trends. Microbiol.* 13: 491-496). Bacteriophages and bacteria may have evolved such that phages have selected immutable target peptidoglycan bonds for cleavage with the endolysin to guarantee escape from the bacterium.

The near-species specificity of phage lysins avoids many pitfalls associated with broad range antimicrobial treatments. Broad range antimicrobials lead to selection for resistant strains, not just in the target pathogen, but also in co-resident commensal bacteria exposed to the drug. The acquisition of antibiotic resistance is often accomplished by transfer of DNA sequences from a resistant strain to a susceptible strain. This transfer is not necessarily species or genus limited, and can lead to commensal bacteria that are both antibiotic resistant and that can serve as carriers of these DNA elements for propagation to neighboring bacteria. Those neighboring strains (potential pathogens) with newly acquired resistance elements can emerge as antibiotic resistant strains during future treatment episodes. Thus, in order to reduce the spread of antibiotic resistance, it is recommended to avoid subjecting commensal bacterial communities to broad range antibiotics. Toward this end, FDA, USDA, and CDC promote the development of antimicrobials that reduce the risk of resistance development (CDC Action Plan: Retrieved from the Internet: .cdc.gov/druq resistance/actionplan).

Endolysins with two active domains are expected to be more refractory to resistance development since the cell will need to mutate or modify multiple target bonds to resist the lytic action of two activities (Fischetti, supra). The use of two bacteriophage endolysins has been reported to have a synergistic effect in the killing of streptococcal pathogens both in vitro (Loeffler et al. 2003. *Antimicrob. Agents Chemother.* 47: 375-377) and in vivo in a mouse sepsis model (Jado et al. 2003. *J. Antimicrob. Chemother.* 52: 967-973). This is consistent with synergy and better cure rates observed in models of *S. aureus* infections in which animals are treated with either antibiotics or Lysostaphin plus an antibiotic (Climo et al. 1998. *Antimicrob. Agents Chemother.* 42: 1355-1360; Climo et al. 2001, supra). Synergistic bactericidal activity has also been demonstrated with an endolysin and an antibiotic against *S. pneumoniae* (Djurkovic et al. 2005. *Antimicrob. Agents Chemother.* 49: 1225-1228).). A recent patent application (Kokai-Kun, J. F. 2003. US 20030211995) indicates there is synergy with Lysostaphin and the phi11 endolysin or the antibiotic bacitracin against *S. aureus*.

Lysostaphin or endolysin injections can cure bacterial infections and do not raise an adverse immune response. It has been reported that Lysostaphin was efficacious in treating *S. aureus* animal infections, but the preparation was likely contaminated with other bacterial antigens, and actual doses were probably less than those described in the 1960s (reviewed in (Climo et al. 1998, supra). Lysostaphin has also been used to treat bovine mastitis (Oldham and Daly. 1991. *J. Dairy Sci.* 74: 4175-4182). The treatment effectively cleared the milk of *S. aureus*, and no deleterious effects to the animals were reported. Nonetheless, the majority of Lysostaphin-treated quarters relapsed after treatment ceased.

Peptidoglycan hydrolases have been proposed for human antimicrobial applications (Fischetti, V. A. 2003. *Ann. N.Y. Acad. Sci.* 987: 207-214; Fischetti 2005, supra; Schuch et al., supra), and they have demonstrated efficacy in animal models for eliminating Group B streptococcal colonization (Cheng et al. 2005. *Antimicrob. Agents Chemother.* 49: 111-117; Nelson et al. 2001. *Proc. Natl. Acad. Sci. USA* 98: 4107-4112), pneumococcal sepsis (Jado et al., supra), and *S. aureus* infection of mammary glands in transgenic mice (Kerr et al. 2001. *Nat. Biotechnol.* 19: 66-70) and cows (Wall et al. 2005. *Nat. Biotechnol.* 23: 445-451). Lysostaphin significantly increased survival of neonatal rat pups when given intravenously (IV) at either 30 or 60 min post *S. aureus* challenge (Oluola et al. 2007. *Antimicrob. Agents Chemother.* 51: 2198-2200). In a recent catheter-induced *S. aureus* endocarditis model, Lysostaphin was tolerated by the systemic route with minimal adverse effects (Climo et al. 1998, supra). Rabbits injected weekly with Lysostaphin (15 mg/kg) for 9 wks by the IV route produced serum antibodies that resulted in an eight-fold reduction in its lytic activity, consistent with earlier work (Schaffner et al. 1967. *Yale J. Biol. Med.* 39: 230-244), but no adverse immune response. It is believed that high purity and the absence of Gram-negative lipopolysaccharide are essential for guaranteeing a minimal host immune response.

Serum antibodies raised to phage endolysins specific to *Bacillus anthracis, Streptococcus pyogenes*, or *Streptococcus pneumoniae* slowed but did not block in vitro killing of the organism in vivo (Fischetti 2005, supra; Loeffler et al. 2003, supra). Cpl-1, a *S. pneumoniae*-specific phage lysin, was injected IV 3 times per week into mice for 4 wks, and 5 of 6 mice tested positive for IgG antibodies to Cpl-1. Vaccinated and naive mice were then challenged IV with pneumococci, and the mice were treated IV with 200 µg Cpl-1 after 10 h. Bacteremia was reduced within 1 min to the same level in both mouse groups, indicating that the antibody did not neutralize the enzyme in vivo (Loeffler et al. 2003, supra). Western blot analysis revealed that Cpl-1 and Pal elicited antibodies 10 d after a 200-µg injection in mice, but the second injection (at 20 d) also reduced the bacteremia profile 2-3 log units, indicating that the antibodies were not neutralizing in vivo. All mice recovered fully with no apparent adverse side effects or anaphylaxis (Jado et al. 2003, supra). A bacteriophage lysin also cleared streptococci from the blood of rats in an experimental endocarditis model, although antibody production was not monitored in this study (Entenza et al. 2005. *Infect. Immun.* 73: 990-998). Similarly, aqueous preparations of phage lysins have been proposed for the control of pathogenic bacteria on human mucous membranes (Fischetti 2003, supra) and mucosal clearing has been obtained with phage lytic enzymes applied to the murine vagina, oropharynx (Cheng et al. 2005, supra), and oral cavity (Nelson et al., supra). The mucosal immune response to these enzymes was not monitored in any of these studies.

Thus, *S. aureus* is a significant pathogen in both agricultural and human disease. Multi-drug resistant strains have become more prevalent, especially nosocomial and community acquired strains, and current antibiotic treatments are often less than 50% effective. This increased incidence of bacterial antibiotic resistance has led to a renewed search for novel antimicrobials that are refractory to resistance development.

SUMMARY OF THE INVENTION

We have discovered that a triple fusion antimicrobial protein comprising three different peptidoglycan hydrolase domains each of which specifically attacks the peptidoglycan cell wall of live, untreated *S. aureus* from without, each of which cuts the peptidoglycan at a different, unique covalent bond of the peptidoglycan, and each of which is lytic in the presence of lysis by the others, is a novel antimicrobial polypeptide for the treatment of infections and disease caused by *S. aureus*.

In accordance with this discovery, it is an object of the invention to provide a triple fusion antimicrobial protein comprising three different peptidoglycan hydrolase domains each of which specifically attacks the peptidoglycan cell wall of live, untreated *S. aureus* from without, each of which cuts the peptidoglycan at a different, unique covalent bond of the peptidoglycan, and each of which is lytic in the presence of lysis by the others.

It is also an object of the invention to provide a recombinant nucleic acid encoding a triple fusion antimicrobial protein comprising three different peptidoglycan hydrolase domains each of which specifically attacks the peptidoglycan cell wall of live, untreated *S. aureus* from without, each of which cuts the peptidoglycan at a different, unique covalent bond of the peptidoglycan, and each of which is lytic in the presence of lysis by the others.

It is another object of the invention to provide a triple fusion antimicrobial protein comprising three different peptidoglycan hydrolase domains, the parental lysins of each having been shown to be synergistic in their antimicrobial activity, and the nucleic acid encoding the triple fusion protein.

It is a further object of the invention to provide an antimicrobial LysK endolysin-Lysostaphin triple fusion protein, comprising (1) a LysK CHAP endopeptidase, (2) a LysK amidase, and (3) a Lysostaphin glycyl-glycine endopeptidase domain, in which all three lytic domains are functional, i.e., degrades the peptidoglycan cell wall of untreated, live *Staphylococcus aureus*; and the nucleic acid encoding the protein.

It is another object of the invention to provide an antimicrobial phi11 endolysin-Lyso triple fusion protein, comprising a (1) phi11 CHAP endopeptidase, (2) a phi11 amidase, and (3) a Lysostaphin glycyl-glycine endopeptidase domain, in which all three lytic domains are functional, i.e., degrades the peptidoglycan cell wall of untreated, live *Staphylococcus aureus*; and the nucleic acid encoding the protein.

An added object of the invention is to provide a pharmaceutical composition comprising the triple fusion polypeptides according to the invention, each which allows *Staphylococcus*-induced disease and infection to be treated.

An added object of the invention is to provide compositions useful for the treatment of diseases and infections caused by the bacteria for which the LysK endolysin and Lysostaphin are specific where the composition comprises a triple fusion polypeptide having three peptidoglycan hydrolase domains each of which retains its property of effectively lysing said bacteria.

An added object of the invention is method of treating diseases and infections with the triple fusion polypeptide of the invention, wherein said diseases and infections are caused by the bacteria for which the three peptidoglycan hydrolases of the triple fusion protein are specific.

A further object of the invention is method of using the triple fusion polypeptide of the invention to kill *S. aureus* in biofilms.

Also part of this invention is a kit, comprising a composition for treatment of disease caused by the bacteria for which the LysK endolysin and Lysostaphin are specific.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

Gly Gly Gly Gly Gly and Ala Gln LyS Ala Gly are identified by SEQ ID NO:34 and SEQ ID NO:35, respectively.

Figure 2:
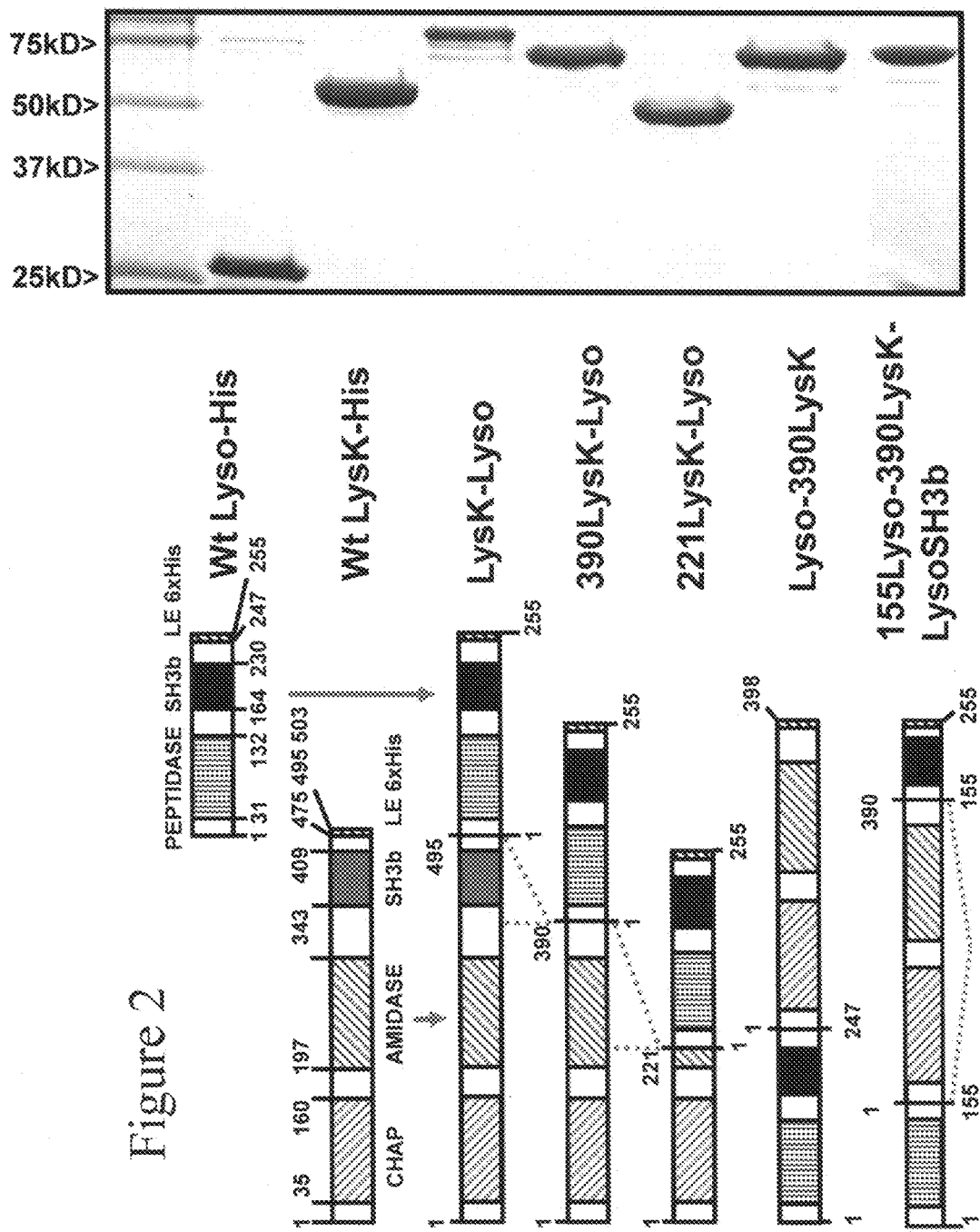

FIG. 2 is a schematic of five fusion construct preparations and the two parental peptidoglycan hydrolase enzymes from which some of the fusions were derived. Each protein is purified via nickel column chromatography that takes advantage of an engineered C-terminal 6×His tag (white stripes). A pair of amino acids (LE) are introduced into each construct at the XhoI Restriction enzyme site immediately prior to the addition of the 6×His tag. His-tagged wild type Lysostaphin (Lyso-His; SEQ ID NO:2) has just one (glycyl-glycine) endopeptidase domain (blue) and a SH3b cell wall binding domain (black). His-tagged wild type LysK (Wt LysK-His; SEQ ID NO:4) has a C-terminal SH3b cell wall binding domain (grey) and two lytic domains, a CHAP endopeptidase (red) and an amidase domain (green). Various fusions between LysK and Lysostaphin have been created, wherein the domain order is shuffled or deleted, and small restriction site sequences are inserted at some fusion junctions. LysK-Lyso (SEQ ID NO:6) is a fusion of both full length proteins with a C-terminal His-tag. 390LysK-Lyso (SEQ ID NO:8) is derived from the LysK-Lyso fusion but lacks the LysK SH3b domain. 221LysK-Lyso (SEQ ID NO:10) is lacking both the LysK SH3b domain and 122 amino acids of the LysK amidase domain. Lyso-390LysK (SEQ ID NO:12) is the reverse orientation as 390LysK-Lyso and is also lacking the LysK Sh3b domain. 155Lyso-390LysK-LysoSH3b is derived from an insertion of 390-LysK (less the initial methionine) into Lysostaphin at amino acid 156. SDS PAGE depicts 5 µg of the nickel purified fusion proteins in each lane and 32 µg of Kaliedoscope prestained protein ladder sizing markers (Biorad).

Figure 3:
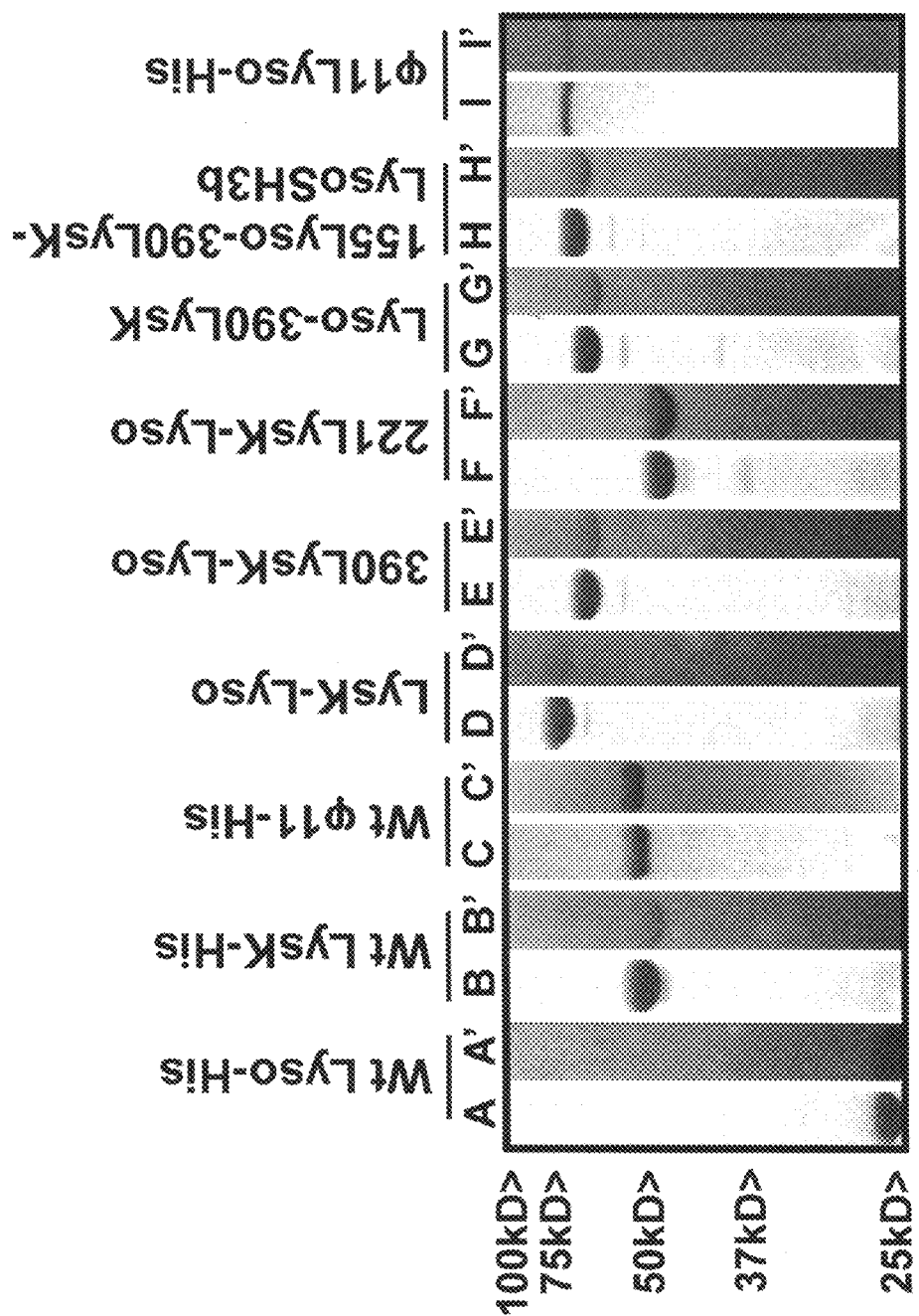

FIG. 3 depicts the SDS PAGE and zymogram of selected purified peptidoglycan hydrolases and fusion constructs. All samples were isolated from plasmid bearing E. coli cultures and purified via nickel chromatography. Zymogram analysis with S. aureus (ATCC 29740) cells embedded in the gel. SDS PAGE gel lanes are presented with corresponding zymogram lanes (indicated as prime). Each well contains 5 µg of purified protein. Lanes A and A', Lysostaphin; Lanes B and B', LysK endolysin; Lanes C and C', φ11; Lanes D and D', LysK-Lyso fusion; Lanes E and E', 390LysK-Lyso fusion; Lanes F and F', 221 LysK-Lyso fusion; Lanes G and G', Lyso-390LysK fusion; Lanes H and H', 155Lyso-390LysK-LysoSh3b fusion; Lanes I and I', φ11-Lyso fusion. The size of the proteins is: Lysostaphin, 66 amino acids, MW=28.1 kD; LysK, 503 amino acids, MW=55.8 kD; phi11 endolysin, 489 amino acids, MW=55.1 kD; LysK-Lyso fusion, 751 amino acids, MW=83.0 kD; 390LysK-Lyso, 673 amino acids, MW=71.4 kD; 221 LysK-Lyso, 477 amino acids, MW=52.9 kD; Lyso-390LysK, 646 amino acids, MW=71.6 kD; 155Lyso-390LysK-LysoSH3b (SEQ ID NO:30), 646 amino acids, MW+71.6 kD; phi11-Lyso fusion, 677 amino acids, MW=75.4 kD.

Figure 4:
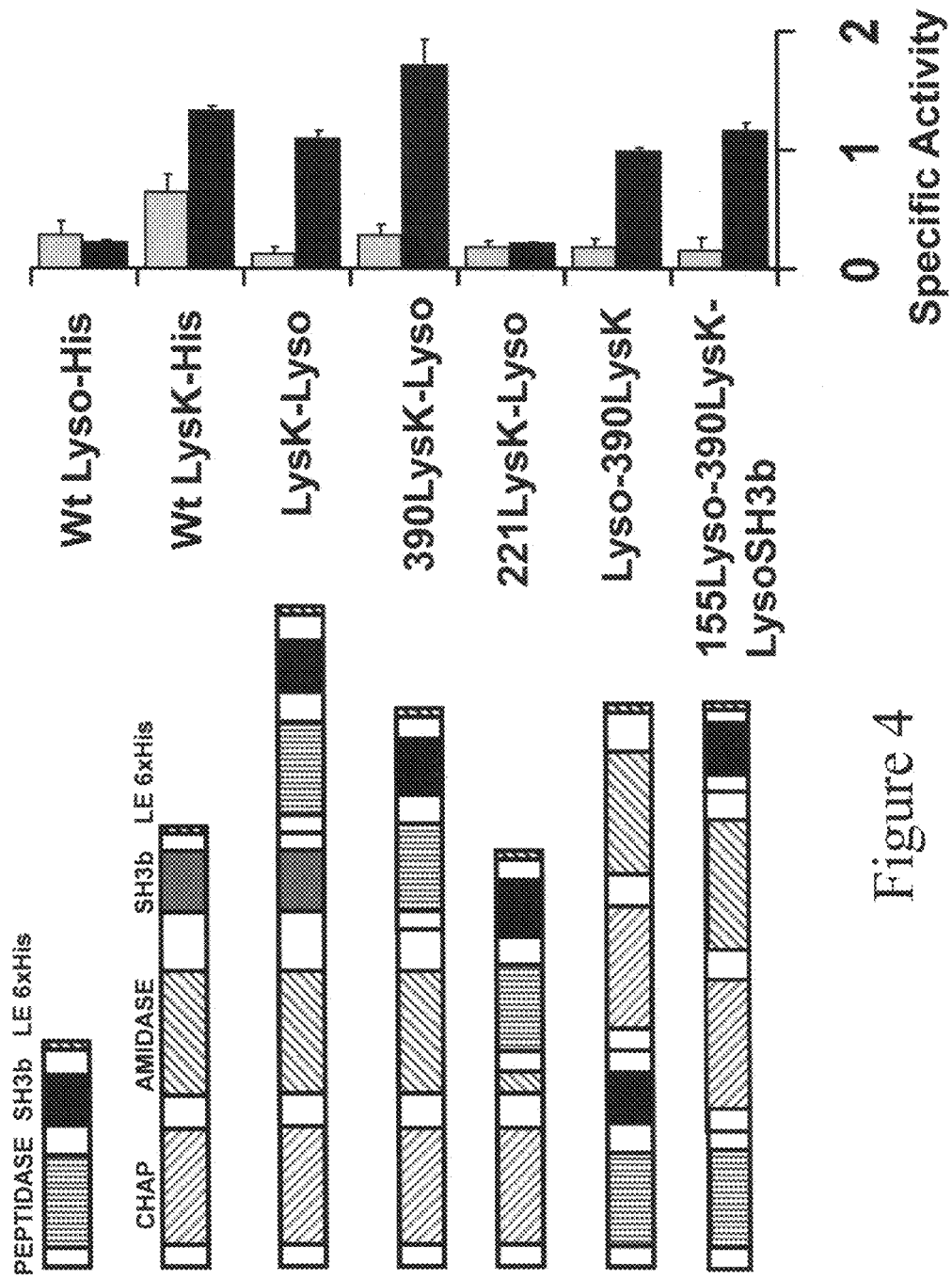

FIG. 4 depicts results of turbidity reduction assays with four of the fusion proteins and two of the parental lysins. S. aureus Newman was grown to log phase (0.4-0.6 $OD_{600\ nm}$), pelleted, and suspended in 150 mM NaCl, 20 mM Tris pH 7.5 30% glycerol and frozen at −80 degrees Celsius until time of assay. At the time of assay, cells were thawed, washed twice with assay buffer, then resuspended in assay buffer. The assay buffers were either 150 mM NaCl, 20 mM Tris pH 7.5 (grey bars) or 300 mM NaCl, 20 mM Tris pH 7.5 (black bars). 100 µl of the bacterial suspension was added to 5 µg of enzyme in 100 µl buffer in a 96 well plate for an initial $OD_{600\ nm}$ of 1.0. The ODs were measured at 20 sec intervals over 5 min. The maximal activity in each assay for a 40 second interval is reported with error bars representing SEM across 3 experiments, each with 3 replicates. To make comparisons between molecules with different molecular weights, the specific activities of each enzyme ($OD_{600\ nm}$/µg protein) were corrected for the molarity of the enzyme solution ($\Delta OD_{600\ nm}$/min/microMolarity).

Figure 5:
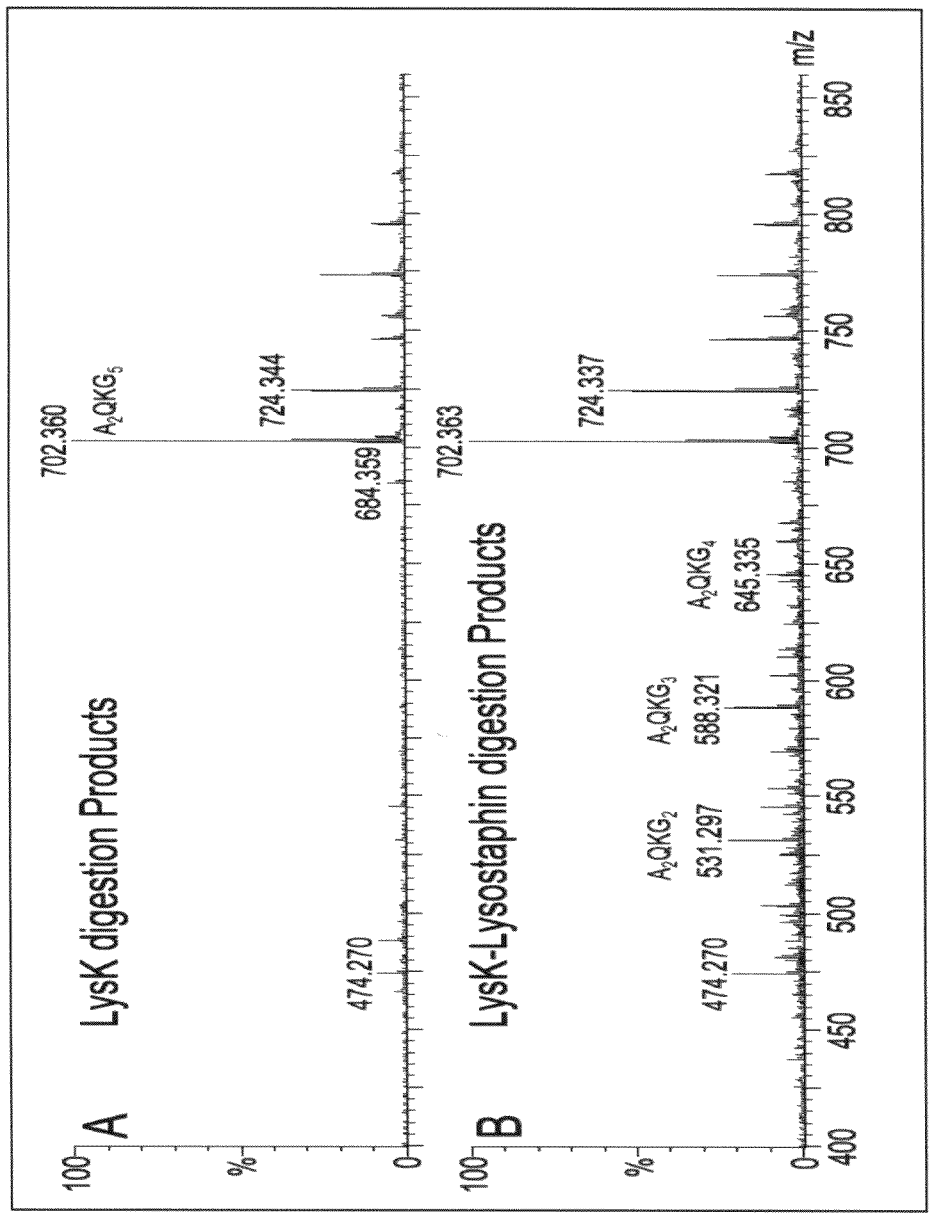

FIGS. 5A and B depict electrospray ionization mass spectra of S. aureus peptidoglycan fragments resulting from digestion with (A) LysK or (B) LysK-Lyso.

Figure 6:
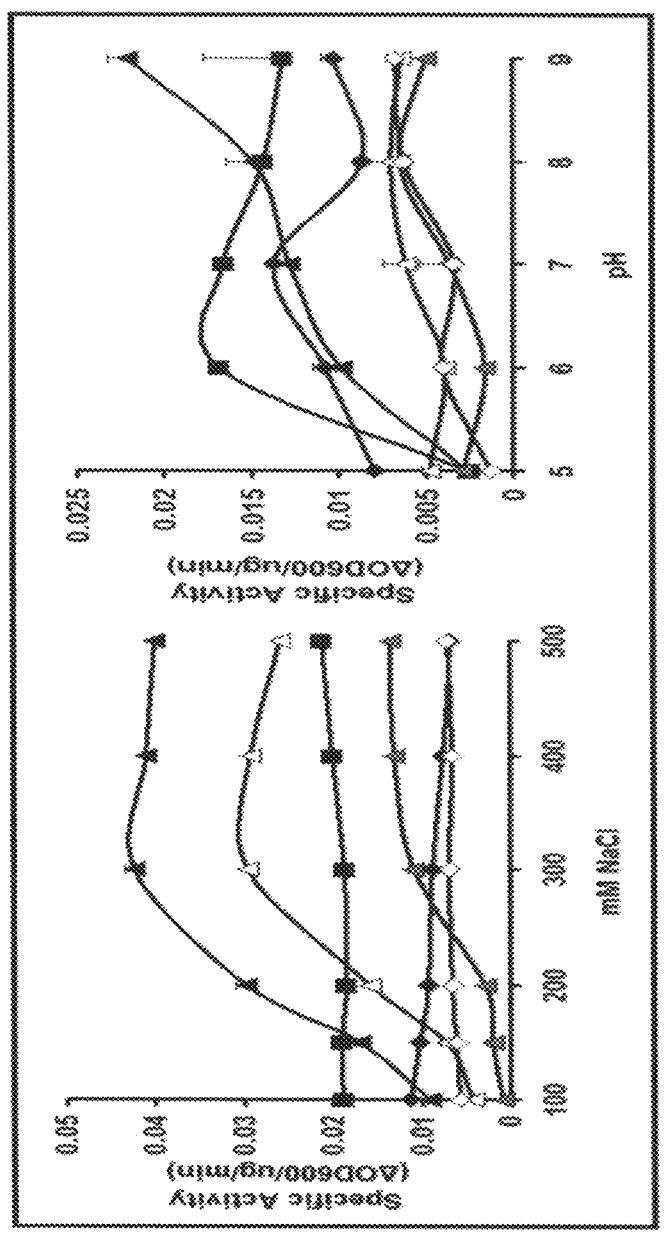

FIG. 6 depicts the effect of salt and pH on lytic activity of endolysins, Lysostaphin and fusion constructs in the turbidity reduction assay. 10 µg of each protein were added to freshly grown, untreated S. aureus Newman strain resuspended in buffers containing various salt concentrations at pH7.5 or various pH buffers containing 150 mM NaCl. Black squares (■) represent Lysostaphin, black triangles (▲) represent LysK, grey triangles (▲) represent the LysK-Lyso fusion, open triangles (Δ) represent the 390K-Lyso fusion, black diamonds (♦) represent the Phi11 endolysin, and open diamonds (◇) represent the Phi11 endolysin-Lyso fusion. 100 µl of cell resuspension was added to 100 µl of enzyme and buffer in a 96 well plate to reach an initial $OD_{600\ nm}$ of 1.0. Each sample is repeated in triplicate and the OD is measured in 20 second intervals for 5 minutes. The maximal activity in each assay, for a 40 second interval, is reported as $\Delta OD_{600\ nm}$/min/µg, with error bars representing standard deviation across experiments.

Figure 7:
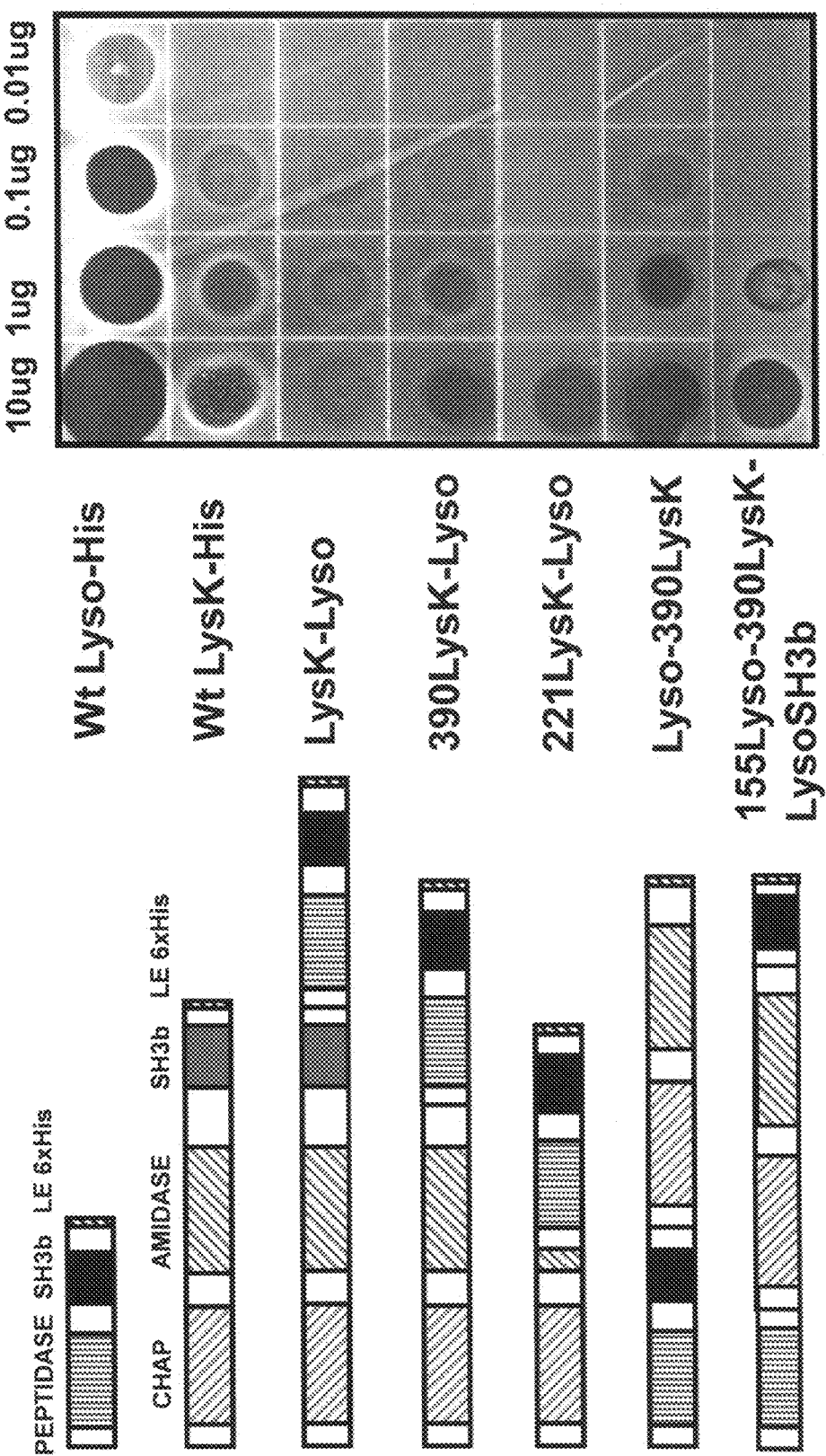

FIG. 7 depicts the results of the fusion proteins in plate lysis assays with S. aureus strain Newman. Purified fusion enzymes were serially diluted to yield concentrations of 10, 1, 0.1, and 0.01 µg/10 µl. 10 µl of each dilution was spotted onto TSB agar plates which were previously irrigated with 2 mL of mid-log (0.4-0.6 $OD_{600\ nm}$) S. aureus strain Newman, excess culture removed, and plates allowed to air dry at room temperature for ~30 minutes in a laminar flow hood. Enzyme spots are allowed to air dry and incubated overnight at 37° C. All fusion constructs were effective in killing live S. aureus; Lysostaphin showed the highest activity in the plate lysis assay, lysing cells at 0.01 µg. All other enzymes analyzed show a weaker but similar activity, requiring 0.1 µg to lyse the S. aureus. Lysostaphin is much smaller than the other proteins; therefore, in molar equivalents, there are approximately three times as many Lysostaphin molecules as some of the other fusions e.g. LysK-Lyso.

Figure 8:
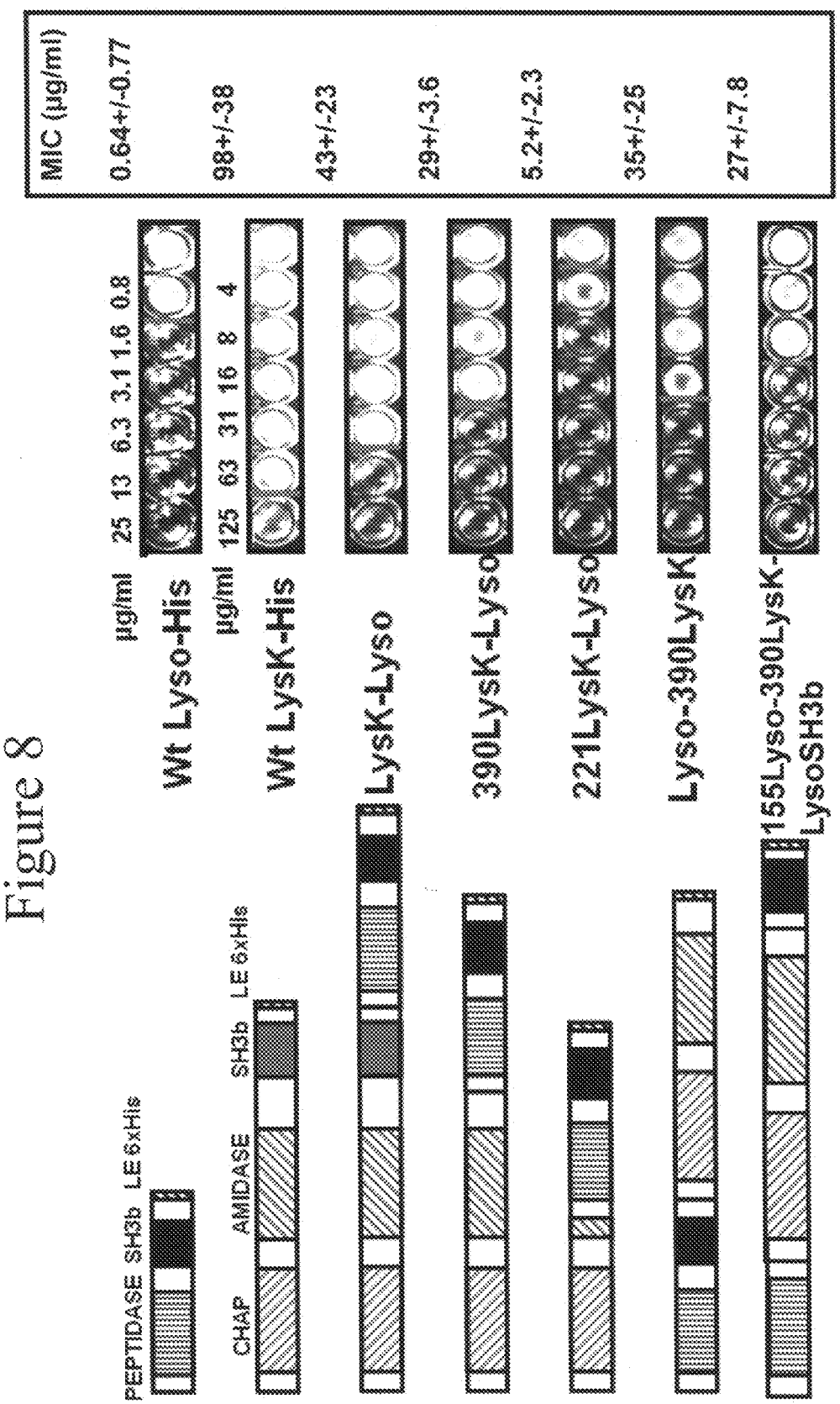

FIG. 8 depicts the Minimum Inhibitory Concentration (MIC) of fusion proteins with S. aureus Newman. Enzymes were first serially diluted two fold across a 96 well plate from the first well containing 100 µl of buffer plus enzyme and 100 µl of 2× sterile Tryptic Soy Broth (TSB). 100 µl of these dilutions are then transferred to duplicate 96 well plates to which 100 µl of S. aureus Newman in TSB is added to each well. The CFU of the inoculating culture is ~5×$10^6$ cells/ml. Plates are incubated 20 hours at 37° C. at which time plates are read with a 96 well plate reader and photographed. Plate reader $OD_{600\ nm}$ values are used to determine the MIC. Wells that have less than 50% $OD_{600}$ of the full growth (bright wells) are considered growth inhibited (red lines). Lysostaphin is serially diluted from 25 µg/ml, all other proteins are serially diluted from 125 µg/ml in the first well. Each well in the final assay contains 200 µl of 1×TSB with the buffer contributing 37.6 mM NaCl and 2.5 mM Tris. All fusion constructs and parental lysins demonstrate the ability to inhibit S. aureus growth; Lysostaphin is again more active than the fusion proteins. The 221K-lyso construct is most active of the fusion proteins, inhibiting culture growth at 5 µg/ml concentration.

Figure 9:
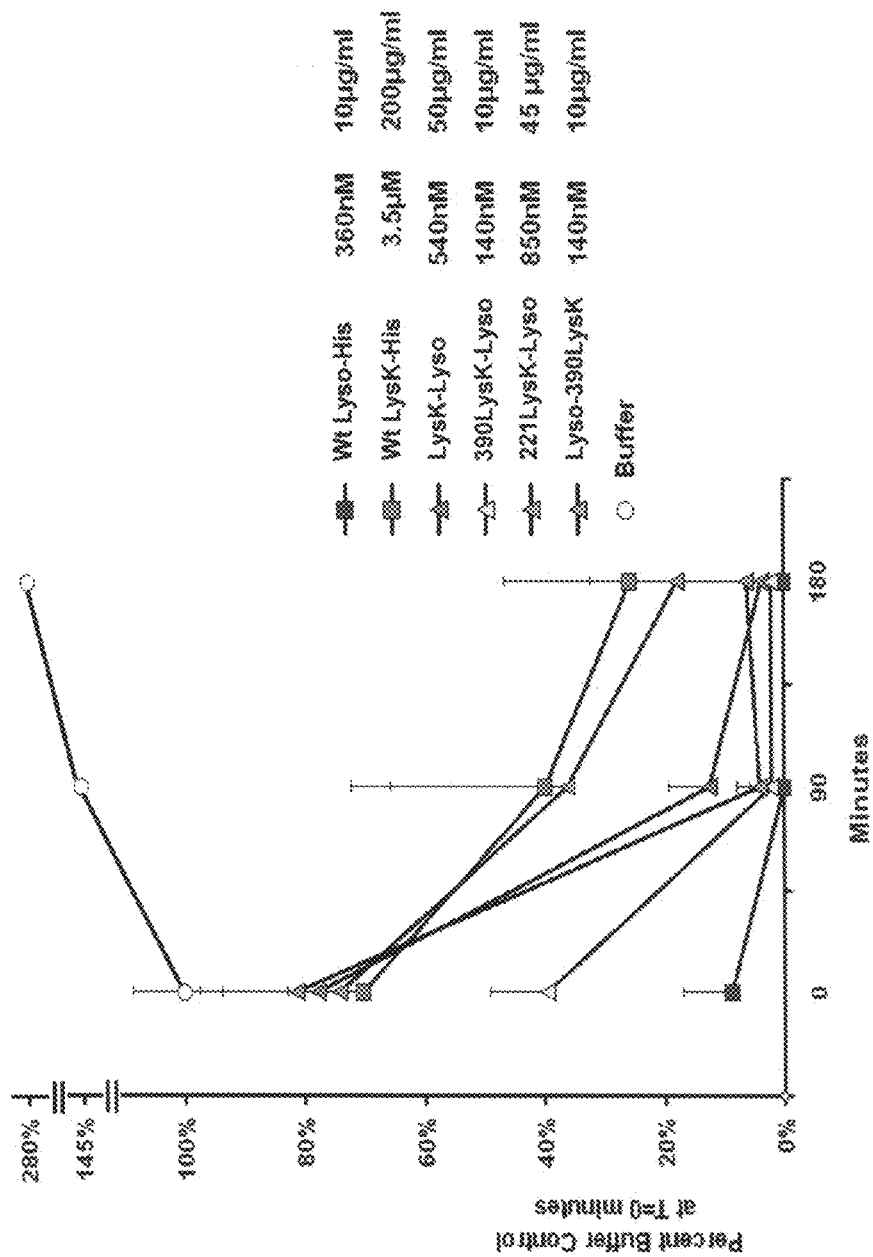

FIG. 9 shows bactericidal activity of fusion proteins in rat blood. CFUs were determined by serial dilution plating of rat blood following various incubation times with buffer alone (control), or various concentrations of each of six lytic enzyme constructs. Data is presented as percent buffer alone control CFUs at the zero minute time point. Note that the amount of enzyme is variable between samples. Blue squares (■) represent Lysostaphin; red squares (■) represent LysK; purple triangles (▲) represent LysK-Lyso fusion; yellow triangles (▲) represent 390LysK-Lyso fusion; green triangles (▲) represent 221 LysK-Lyso fusion; and blue triangles (▲) represent Lyso-390LysK fusion; empty circles (○) represent the buffer only control. (see FIG. 4 for construct schematics). Error bars represent the standard deviation of three replicate experiments.

DETAILED DESCRIPTION OF THE INVENTION

Cell wall peptidoglycan is the major structural component of bacterial cell walls. Bacterial peptidoglycan has a complex structure; namely, a sugar backbone of alternating units of N-acetyl glucosamine (GN) and N-acetyl muramic acid (MN) residues, cross-linked by oligopeptide attachments at the MNs. Bacteriophage endolysins are peptidoglycan hydrolase enzymes synthesized by bacteriophage to help nascent phage escape the host at the end of the lytic cycle. Through digestion of the peptidoglycan, endolysins can lyse host bacterial cells with near species specificity, a characteristic that makes them an excellent source of new antimicrobial agents. It is believed that the phage and host have co-evolved, such that there has been no host identified that can develop resistance to their phage endolysin. Thus, these hydrolases are a novel source of new antimicrobials with an evolutionary proven track record in avoiding host resistance mechanisms. They function from outside the cell thus also reducing the potential resistance mechanisms that most bacterial cells employ. The endolysins digest the host cell walls with near-species specificity. A minimal pathogen target range is a preferred trait in new antimicrobials as a mechanism to reduce the risk of resistance development in non-pathogenic commensal strains as often occurs during broad range antibiotic treatment.

There are several advantages to the use of enzyme antimicrobials compared to conventional antibiotics. Phage endolysins have evolved a modular design to deal with the complex structure of the bacterial cell wall. One protein can harbor multiple domains, including both lytic and cell wall binding domains. Three classes of endolysin domains have been identified thus far: endopeptidase, glycosidase, and amidase. Any one of these domains is sufficient to lyse the bacterial target cell. Each has been localized to short protein domains (~100-200 amino acids). Here, we demonstrate that fusion constructs consisting of three lytic domains, with specificity to just one genus, Staphylococcus, maintain all three peptidoglycan digestion activities in the expressed triple fusion polypeptide. We show that bacteria cannot evade the effects of three unique peptidoglycan hydrolase lytic activities simultaneously. Thus, the triple fusion construct and the resulting triple fusion polypeptide of the invention represent the first class of Gram positive antimicrobials that are refractory to resistance development.

Phi11 hydrolase, LysK and Lysostaphin harbor endopeptidase domains that are examples of peptidoglycan hydrolase endopeptidases that cleave peptide bonds. Glucosaminidases and muramidase are examples of glycosidase that cleave between N-acetyl glucoseamine (GN) and N-acetyl muramice acid (MN). The phi11 and LysK endolysins harbor amidase domains that cleave between the MN and the first amino acid of the peptide region of the peptidoglycan.

We have taken advantage of the modular nature of peptidoglycan hydrolase enzymes to create fusion proteins that harbor three lytic domains and at least one SH3b cell wall binding domain, each targeting the peptidoglycan bonds of a Gram positive pathogen (S. aureus). We have chosen three peptidoglycan hydrolase domains that are known to cleave the peptidoglycan at unique chemical bonds. The first triple fusion was created by the fusion of LysK (endolysin from the phage K) and Lysostaphin (a bacteriocin secreted by Staphylococcus simulans to kill S. aureus). The triple fusion protein, LysK-Lyso (SEQ ID NO: 6) harbors a CHAP endopeptidase, amidase and glycyl-glycine endopeptidase activity. It is generally accepted that no bacteria can avoid the effects of three antimicrobial domains simultaneously, thus we predict and demonstrate (data not shown) that our fusions will be refractory to resistance development. We have also created a second fusion protein, phi11 endolysin-Lysostaphin (phi11-Lyso; SEQ ID NO:14) and find a nearly identical set of results with all three lytic domains active in the final fusion (data not shown).

Peptidoglycan hydrolases are also important new antimicrobials because they have been shown to degrade staphylococcal biofilms. Biofilms are sessile forms of bacterial colonies that attach to a mechanical or prosthetic device or a layer of mammalian cells. NIH estimates that 80% of bacterial infections occur as biofilms (Retrieved from the Internet: grants.nih.gov/grants/guide/pa-files/PA-06-537). Bacteria in biofilms can be orders of magnitude more resistant to antibiotic treatment than their planktonic (liquid culture) counterparts.

Several mechanisms are thought to contribute to the antimicrobial resistance associated with biofilms: 1) delayed or restricted penetration of antimicrobial agents through the biofilm exopolysaccharide matrix, which might serve as a barrier, an adsorbent, or a reactant; 2) decreased metabolism and growth rate of biofilm organisms which resist killing by compounds that only attack actively growing cells; 3) increased accumulation of antimicrobial-degrading enzymes; 4) enhanced exchange rates of genes encoding for resistance; 5) physiological changes due to the biofilm mode of growth, including "persister" cells which appear to have altered their physiology in such a way as to disable programmed cell death; and 6) increased antibiotic tolerance (as opposed to resistance) through expression of stress response genes, phase variation, and biofilm specific phenotype development. Most of these mechanisms are avoided by our peptidoglycan hydrolases that lyse the cell from outside the cell.

Biofilms also show heightened resistance to host defense mechanisms. Cells grown in biofilms express a polymer of beta-1,6-linked N-acetylglucosamine (PNAG) in large amounts. Biofilm cultures are believed to exhibit reduced activation of complement (compared to planktonic cultures), and the aggregation of bacteria makes them less susceptible to phagocytosis. Altered gene expression of binding factors, cell surface peptidoglycan, glycoprotein synthesizing enzymes, and stress related proteins involved in the detoxification of formate, urea and reactive oxygen species, are likely factors involved in persistence and resistance of cells in a biofilm. Treatment with antibiotics, especially subinhibitory concentrations, can actually foster the formation of biofilms. There is clearly a current need for enzymes to break down biofilms for more efficient treatment of biofilm-associated staphylococcal infections.

It is known that Lysostaphin can kill cells in biofilms. Phi11 endolysin was also recently reported to kill staphylococcal cells in biofilms (Sass and Bierbaum. 2007. *Appl. Environ. Microbiol.* 73 (1):347-52). We have also shown that LysK can kill cells in biofilms (data not shown). We anticipate that if all of the components of our triple fusions are known to kill cells in biofilms our triple fusion antimicrobials will be similarly effective.

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding, for example, the LysK-Lyso fusion protein according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

As used herein, "recombinant" refers to a nucleic acid molecule which has been obtained by manipulation of genetic material using restriction enzymes, ligases, and similar genetic engineering techniques as described by, for example, Sambrook et al. 1989. *Molecular Cloning: A Laboratory Manual*, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

A "protein" or "polypeptide" is a chain of amino acids arranged in a specific order determined by the coding sequence in a polynucleotide encoding the polypeptide. Each protein or polypeptide has a unique function.

The invention includes functional LysK-Lyso fusion protein, 390LysK-Lyso fusion protein, 221LysK-Lyso fusion protein, Lyso-390 LysK fusion protein, 155Lyso-390 LysK-LysoSH3b fusion protein, phi11-Lyso fusion protein, and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments" refers to all fragments of the lytic domains of the triple fusion polypeptide of the invention that retain lytic activity and function to lyse staphylococcal bacteria.

Modifications of the primary amino acid sequence of the lytic domains of the invention may result in further mutant or variant proteins having substantially equivalent activity to the fusion polypeptides described herein. Such modifications may be deliberate, as by site-directed mutagenesis, or may occur by spontaneous changes in amino acid sequences where these changes produce modified polypeptides having substantially equivalent activity to the endolysin polypeptides of the triple fusion polypeptide. Any polypeptides produced by minor modifications of the endolysin primary amino acid sequence are included herein as long as the biological activity endolysin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar"

also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a LysK-Lyso fusion polypeptide, 390 LysK-Lyso fusion polypeptide, 221 LysK-Lyso fusion polypeptide, Lyso-390 LysK fusion polypeptide, 155Lyso-390LysK-LysoSH3b fusion polypeptide, phi11-Lyso fusion polypeptide and which hybridize under stringent conditions to the LysK-Lyso fusion polypeptide, 390 LysK-Lyso fusion polypeptide, 221 LysK-Lyso fusion polypeptide, Lyso-390 LysK fusion polypeptide, 155Lyso-390LysK-LysoSH3b fusion polypeptide, phi11-Lyso fusion polypeptide sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have LysK-Lyso fusion polypeptide-, 390 LysK-Lyso fusion polypeptide-, 221 LysK-Lyso fusion polypeptide-, Lyso-390 LysK fusion polypeptide-, 155Lyso-390LysK-LysoSH3b fusion polypeptide-, and phi11-Lyso fusion polypeptide-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the LysK-Lyso fusion polypeptides, 390 LysK-Lyso fusion polypeptides, 221 LysK-Lyso fusion polypeptides, Lyso-390LysK fusion polypeptides, 155Lyso-390LysK-LysoSH3b fusion polypeptide or phi11-Lyso fusion polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, LysK-Lyso fusion protein, 390 LysK-Lyso fusion protein, 221 LysK-Lyso fusion protein, Lyso-390LysK fusion protein, 155Lyso-390LysK-LysoSH3b fusion polypeptide, phi11-Lyso fusion protein activity as described herein. Such variants may result from, for example, genetic polymorphism or from human manipulation. Biologically active variants of a LysK-Lyso fusion polypeptide, 390LysK-Lyso fusion polypeptide, 221LysK-Lyso fusion polypeptide, Lyso-390LysK fusion polypeptide, 155Lyso-390LysK-LysoSH3b fusion polypeptide or phi11-Lyso fusion polypeptide of the invention will have at least about 90%, preferably at least about 95%, and more preferably at least about 98% sequence identity to the amino acid sequence for the protein of the invention as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired LysK-Lyso fusion protein, 390LysK-Lyso fusion protein, 221 LysK-Lyso fusion protein, Lyso-390LysK fusion protein, 155Lyso-390LysK-LysoSH3b fusion polypeptide, and/or phi11-Lyso fusion protein activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of LysK-Lyso fusion protein, 390LysK-Lyso fusion protein, 221LysK-Lyso fusion protein, Lyso-390LysK fusion protein, 155Lyso-390LysK-LysoSH3b fusion polypeptide, and/or phi11-Lyso fusion protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these, or attached to a solid stratum such as colloidal gold. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmids, Constructs and Strains

The LysK cDNA was kindly provided by Paul Ross (O'Flaherty et al. 2005. *J. Bacteriol.* 187: 7161-7164). Phage K genomic sequence has been published (AY176327) and the LysK protein sequence is also available (AAO47477.2) through Genbank. Inducible vector constructs were created in pET21a (EMD Biosciences, San Diego, Calif.) for introduction of a C-terminal His-tag. For cloning into pET21a, the LysK sequences were amplified with primers LysK Nde F (5'-GAGAAATTACATATGGCTAAG ACTC-3'; SEQ ID NO:17) and LysK Xho R (5'-ATGGTGATG CTCGAGTTTGAATACTC C-3'; SEQ ID NO:18, Table 1) (engineered restriction enzyme sites are underlined). [All primers utilized in construct preparation are described in Table I.] PCR subcloning is performed when PCR products are gel purified and digested appropriately with Restriction Enzymes (RE) that recognize and cleave at the engineered sites. The resultant gene fragments are purified over a Micro Bio Spin P30 desalting column (BioRAD, Inc.) and introduced into similarly digested, dephosphorylated and gel purified vector pET21a, via conventional means. At the C-terminus of the C-tagged LysK, there are an additional 2 amino acids corresponding to the XhoI site (Leu-Glu) followed by 6 His residues. The resulting plasmid was termed p3514 (listed in Table 2).

A plasmid harboring the Mature Lysostaphin (gi|153046|gb|M15686.1| STALYS) cDNA was a gift from David Kerr, Univ. Vermont. The entire mature protein coding sequence was amplified using the primers Lyso AA1 NdeI F (5'-ACGTACGTCATATGGCTGCAACACATGAAC ATTCAGCAC; SEQ ID NO:19) and RlysoXhoI (5'-GCGCTACTCGAGACCACCTGCT TTTCCATATC; SEQ ID NO:20) and introduced into pET21a via PCR cloning similar to that described for LysK. The resulting plasmid was termed p5301 with the NdeI site contributing the new ATG translational start site for the protein coding sequences.

LysK-Lyso was generated by amplification of Lysostaphin gene sequences, using plasmid p5301 as template and the primers FlysoSal I (5'-ATCATC GTCGACGCTGCAACACATGAACATTCAGCAC; SEQ ID NO: 21) and RlysoXhoI (5'-GC GCTA CTCGAGACCACCTGCTTTTCCATATC; SEQ ID NO: 20). The Lysostaphin fragment was PCR subcloned into the XhoI linearized LysK expression plasmid p3514. The ligation of XhoI to SalI destroys both RE sites and adds two amino acids to the fusion joint, LD (Leu-Asp) which is present in all fusion constructs. The resulting plasmid was termed p5031.

390LysK-Lyso was created by amplification of the LysK fragment with the primers R lysKCA 390 (5'-GTGGTG CTCGAGACTTGCGCTACTTGTTTTACC; SEQ ID NO: 22) (Xho 1 site) and pET21a XbaI F (5'-GGATAACAATTC-CCCTCTAG; SEQ ID NO: 23), using plasmid p3514 as template. The amplified fragment was RE digested and PCR subcloned into XbaI and XhoI cut pET21a similar to the methods described previously, generating plasmid p5404. The Lysostaphin fragment was amplified with primers FlysoSalI and RlysoXhoI and the amplified fragment was RE digested and then introduced into plasmid p5404 that had been linearized with XhoI generating plasmid pSB1101.

221lysK-Lyso was created by first PCR subcloning the lysK fragment encoding amino acids 1-221 into pET21a. The fragment was generated with the template plasmid p3514 and the primers lysK Chap 221S R (5'-GTATTGCTCGAGTGA AGAACGACCTGC; SEQ ID NO:24) and pET21a XbaI F (5'-GGATAACAATTCCCCTCT AG-3'; SEQ ID NO:23). The resultant fragment was RE digested with XhoI and Xba I and PCR subcloned into pET21a to create plasmid pSB0201. The Lysostaphin fragment was then PCR amplified, with FlysoSalI and RlysoXhoI and the amplified fragment was then PCR subcloned into the XhoI linearized plasmid SB0201, generating plasmid pSB0408.

Lyso-390lysK was generated by introducing the PCR product generated by amplification of the template p3514 with the primers LysK aa1 Sal F (5'-GATATA GTC-GACGCTAAGACTC; SEQ ID NO: 25) pET21a Sty I-R (5'-CGTTTAGAGGCCCC AAGGGGTTATG; SEQ ID NO:26) into the XhoI StyI digested p5301. The resulting plasmid was termed pSB1501

The phi11-Lyso fusion was created first by amplifying the phi11 endolysin gene from the template plasmid pTZ18R (a gift from R. Jayaswal containing the phi11 endolysin on a 3 kb EcoRI fragment) with the primers LytA NdeF (5'-GTG-GCGCAT ATGCAAGCAAAATTAAC; SEQ ID NO:27) and LytA XhoI 481 R (5'-TGACTATGTC CTCGAGACT-GATTTC; SEQ ID NO:28). The resultant PCR product was PCR subcloned into NdeI and XhoI digested pET21a to generate the plasmid pLytA481. (Donovan et al. 2006. *FEMS Microbiol Lett.* 265(1):133-239). The Lysostaphin gene was then PCR amplified with the primers FlysoSalI and RlysoXhoI and was PCR subcloned into plasmid pLytA481 via the XhoI site to generate the plasmid p5809. This fusion is a direct fusion of the phi11 endolysin (481 amino acids) and mature Lysostaphin (246 amino acids) open reading frames, in a head to tail, head to tail fusion.

The 155Lyso-390LysK-LysoSH3b fusion was created by first PCR-amplifying the Lysostaphin gene from the template 5301 with the primers LysoAD 155xHO R (5'GTTTGTCTC- GAGACCTGTATTCGG-3'SEQ ID: 31) and Lyso AA1 NdeI F (5'-ACGTACGTCATATGGCTGCAACACAT-GAACATTCAGCAC-3', SEQ ID NO: 19) and introducing this fragment into NdeI XhoI digested pET21a generating pSB1701. A second intermediate was produced by introducing the Lysostaphin SH3b domain to the construct p5404 by amplification of the template 5301 with the primers LysoSH3b SalI F GCGCATCTCGAGACAGTAACTC-CAACGCCG, SEQ ID NO: 32) pET21a Sty I-R (5'-CGTT-TAGAGGCCCC AAGGGGTTATG; SEQ ID NO: 26) and introducing the fragment into XhoI StyI linearized p5404 generating plasmid pSB1001. The final construct 155Lyso-390LysK-LysoSH3b was generated by introducing the PCR product generated by amplification of the template pSB1001 with the primers LysK aa1 Sal F (5'-GATATA GTC-GACGCTAAGACTC; SEQ ID NO: 25) pET21a Sty I-R (5'-CGTTTAGAGGCCCC AAGGGGTTATG; SEQ ID NO: 26) into the XhoI StyI digested pSB1701 generating pSB1801.

All subcloning was performed in *E. coli* DH5a (Invitrogen, Carlsbad, Calif.) for plasmid DNA isolation. All constructs were sequence verified. All constructs were DNA sequence verified. pET21a constructs were induced in *E. coli* BL21 (DE3) (EMD Biosciences, San Diego, Calif.).

TABLE 1

PCR primers utilized to create the fusion constructs.

| Name | Sequence | SEQ ID NO: |
|---|---|---|
| Lyso AA1 NdeI F | ACGTACGTCATATGGCTGCAACACATGAACA TTCAGCAC | 19 |
| RlysoXhoI | GCGCTACTCGAGACCACCTGCTTTTCCATAT C | 20 |
| Lyso Sal I - F | ATCATCGTCGACGCTGCAACACATGAACATT CAGCAC | 21 |
| LysK Nde F | GAGAAATTACATATGGCTAAGACTC | 17 |
| LysK Xho R | ATGGTGATGCTCGAGTTTGAATACTCC | 18 |
| lysK Chap 221SR | GTATTGCTCGAGTGAAGAACGACCTGC | 24 |
| R lysKCA 390 | GTGGTGCTCGAGACTTGCGCTACTTGTTTTA CC | 22 |
| pET21a xbaI F | GGATAACAATTCCCCTCTAG | 23 |
| LysK aa1 Sal F | GATATAGTCGACGCTAAGACTC | 25 |
| pET21a Sty I - R | CGTTTAGAGGCCCCAAGGGGTTATG | 26 |
| LytA NdeF | GTGGCGCATATGCAAGCAAAATTAAC | 27 |
| LytA XhoI 481 R | TGACTATGTCCTCGAGACTGATTTC | 28 |
| LysoSH3b SalI F | GCGCATCTCGAGACAGTAACTCCAACGCCG | 32 |

Bolded sequences represent Restriction Enzyme sequences utilized in the cloning protocol.

TABLE 2

Inducible plasmids used during construction of, and expression of, fusion constructs.

| Plasmid | Construct |
|---|---|
| p3514 | LysK |
| p5301 | Lysostaphin |

TABLE 2-continued

Inducible plasmids used during construction of, and expression of, fusion constructs.

| Plasmid | Construct |
|---|---|
| p5031 | LysK-Lyso |
| p5404 | 390LysK |
| pSB1101 | 390LysK-Lyso |
| pSB0201 | 221LysK |
| pSB0408 | 221LysK-Lyso |
| pSB1501 | Lyso-390LysK |
| pSB1801 | 155Lyso-390LysK-LysoSH3b |
| pLytA481 | Phi11 |
| p5809 | Phi11-Lyso |

*Staphylococcus aureus* Newbolt 305 capsular polysaccharide serotype 5 (ATCC 29740) and *Staphylococcus* Newman (gift from Jean Lee, Harvard Univ.) were grown at 37° C. in Brain Heart Infusion broth (BD, Sparks, Md.) or Tryptic Soy Broth (BD, Sparks, Md.).

Example 2

Protein Purification

*E. coli* cultures harboring pET21a derived Lysostaphin expression vectors were grown under ampicillin selection to mid log phase ($OD_{600\ nm}$ of 0.4-0.6), chilled on ice for 30 min, induced with 1 mM IPTG (isopropyl-beta-D-thiogalactopyranoside), and incubated at 19° C. with shaking for 18 h. *E. coli* harvested from 100 ml cultures were suspended in 2 ml lysis buffer (50 mM $NaH_2PO_4$, 300 mM NaCl, 10 mM imidazole, pH 8), sonicated on ice for 15×5 sec pulses separated by 15 sec. rests, and centrifuged at 11,000×g for 20 minutes at 4° C. The cleared lysate was transferred to microfuge tubes and centrifuged at 16,000×g for 30 min at 4° C. The cleared supernatant was applied to 1 ml Ni-NTA (nickel matrix) in a slurry and mixed gently for 1 hour at 4° C. (Qiagen). The slurry was loaded into a polypropylene column (Qiagen #34964) where wash and elution buffer profiles were empirically determined for the LysK constructs to be 10 ml of 10 mM imidazole, 20 ml of 20 mM imidazole and elution with 1.2 ml of 250 mM imidazole in the same phosphate buffered saline (50 mM $NaH_2PO_4$, 300 mM NaCl, pH 8.0). Immediately after purification from the nickel column, all samples were brought to 1% glycerol to prevent precipitation of the purified protein. Addition of 1% glycerol has become a routine practice in this lab when isolating His-tagged proteins in order to help resolve solubility issues faced with other His-tagged proteins. All samples were then converted to LysK storage buffer (400 mM NaCl, 20 mM Tris HCl, 1% glycerol, pH 7.5) via Micro Bio Spin P30 desalting column (BioRAD, Inc.) or Zeba desalting column (Pierce) that had been converted to LysK Storage buffer. All samples were then 0.22 micron filter sterilized for use in the MIC assays. After filtration, protein concentration determinations were made via BCA Protein kit (Pierce) and DTT was added to 10 mM after protein concentration determination. Sterilized protein preparations were stored at −80° C. or 4° C. until the time of the assay. Purity of each preparation was determined via SDS-PAGE (FIG. 2). Non-tagged Lysostaphin was purchased (recombinant, Sigma-Aldrich, L0761).

Example 3

SDS PAGE and Zymogram

The purified fusion proteins and Kaleidoscope protein standards (Invitrogen, Carlsbad, Calif.) were analyzed with 15% SDS-PAGE, with or without 300 ml equivalent of mid log phase *S. aureus* 305 cells ($OD_{600\,nm}$ of 0.4-0.6). Gels were prepared and electrophoresed in Tris-Glycine buffer at 100 volts for 1.5 hours in the BioRad Mini-PROTEAN 3 gel apparatus, according to manufacturer's instructions. SDS gels were stained in BioSafe Coomassie stain (BioRad, Hercules, Calif.) for one hour and then rinsed in distilled water overnight. Zymograms were washed in excess water for 1 hour to remove the SDS and incubated at room temperature in water, resulting in areas of clearing in the turbid gel wherever a lytic protein was localized.

Zymogram analysis was performed with a 50× concentrated suspension of log phase *S. aureus* cells added to the SDS PAGE gel mixture prior to polymerization. The SDS PAGE and zymogram gels were made identically, loaded with identical samples, and electrophoresed for the same period of time. The gel results indicate that the protein preparations are >95% pure.

As shown in FIG. 3, 5 µg of the phi11 endolysin, LysK endolysins, LysK-Lysostaphin fusions and the phi11 endolysin-Lyso fusion or 5 µg Lysostaphin produced cleared regions in the zymogram (representing lysis of the *S. aureus* cells embedded in the gel). The position of these cleared zones corresponds to the observed (and predicted) position of the peptidoglycan hydrolase proteins seen in the Coomassie blue-stained SDS-PAGE gel.

Example 4

Catalytic Activity of the Three Domains of the Triple Fusion Lysins

Figure 1:
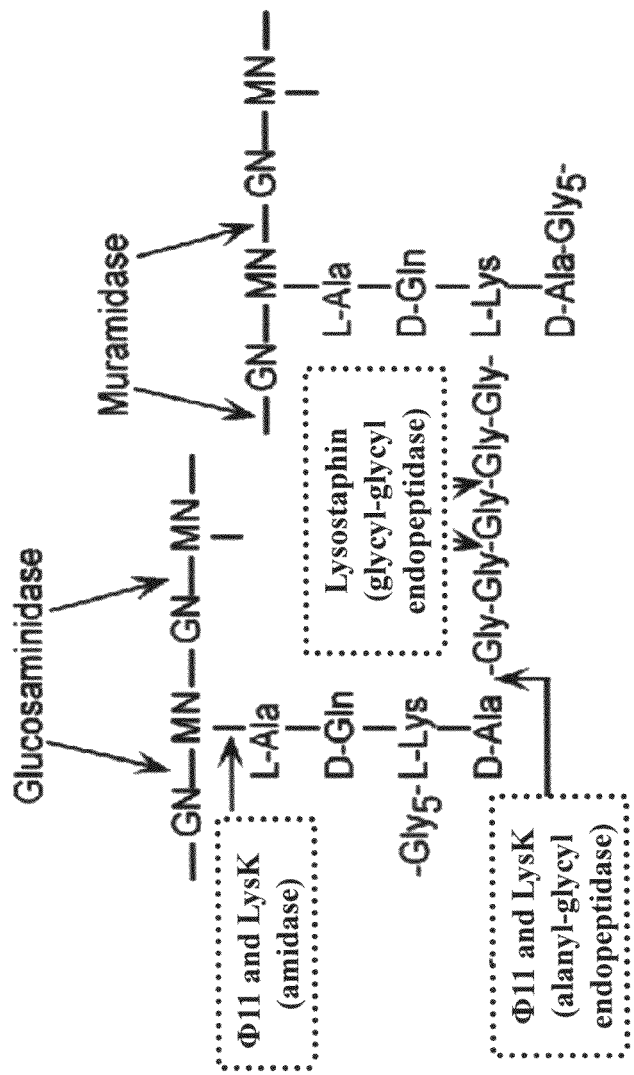
FIG. 1 shows the peptidoglycan structure and sites of hydrolase cleavage. Phi11 hydrolase and Lysostaphin contain domains encoding peptidoglycan endopeptidases. The Phi11 hydrolase also has an amidase activity cleaving between the sugar backbone and the first alanine of SEQ ID NO:33 (Ala Gin Lys Ala). LysK cleaves in the exact same locations as the phi11 endolysin (data described below FIG. 5). Glucosaminidase and muramidase are examples of glycosidases that cleave between N-acetyl glucosamine (GN) and N-acetyl muramic acid (MN). Amidases cleave between the MN and the first amino acid of the peptide. Gram positive cell walls can have up to 40 layers of this sugar-protein structure [adapted from (Navarre et al. 1999. *J. Biol. Chem.* 274: 15847-15856)]. Two additional peptide sequences shown, i.e.

We assessed the relative lytic contributions of the three different domains of the triple fusion constructs to determine the activity of all the domains and also to determine that the products resulting from a given domain's activity were suitable substrates for the catalytic activities of the other two domains. Our approach to identifying active lytic domains in the lysin constructs is to analyze the cell wall digestion products. An increase in reducing activity of the reaction products during digestion indicates glycosidase activity. Analysis of the sodium borohydride reduction products of the digests allows us to determine if the glycosidase is an N-acetylglucosaminidase or an N-acetylmuramidase. Using such a procedure previously, indicated that the B30 lysin possesses N-acetylmuramidase activity (Baker et al. 2006. *Appl. Environ. Microbiol.* 72: 6825-6828; Pritchard et al. 2004, supra) and the LambdaSa2 lysin has N-acetyl-glucosaminidase activity (Pritchard et al. 2007. *Appl. Environ. Microbiol.* 73: 7150-7154). We analyzed the LysK, the LysK-Lyso, and 390Lysk-Lyso enzyme digestion products with electrospray ionization mass spectrometry (ESI-MS) (sometimes coupled to HPLC) to detect amidase and endopeptidase activities. In addition, we used synthetic peptide substrates that mimic the stem peptide and cross bridges of peptidoglycan to confirm the endopeptidase cleavage sites. For example, using synthetic peptides, we were able to show that the endopeptidase of the B30 lysin cleaves between the D-Ala of the stem peptide and the L-Ala of the cross bridge (Baker et al., supra; Pritchard et al. 2004, supra). Similar methods were used to demonstrate gamma-D-glutaminyl-L-lysine activity in the LambdaSa2 lysin (Pritchard et al. 2007, supra). We have also determined the peptidoglycan cut sites for LysK, which are identical to the phi11 endolysin (FIG. 1).

When the full length phi11-Lyso (data not shown), LysK-Lyso (FIG. 5B), and 390Lysk-Lyso (data not shown) triple fusions were tested using ESI-MS for cut site determination, all 3 domains were active in all three constructs. Characterization of the peptide products in cell wall digests of LysK resulted in the identification of the two enzymatically active peptidoglycan lytic domains. One is an amidase that cleaves between N-acetylmuramic acid residues and L-alanine of the stem peptide, and the other is an endopeptidase that cleaves between a D-alanine in the stem peptide and a glycine in the cross-bridge peptide. Similar activities have been reported for the phi11 lysin (Navarre et al. 1999. *J. Biol. Chem.* 274: 15847-15856). The primary product of LysK digestion was $A_2QKG_5$, which in positive-ion ESI-MS gives a peak with a m/z=702 (FIG. 5A). Lysostaphin cleaves staphylococcal peptidoglycan between the second and third, and third and fourth, glycine residues of the cross-bridges. ESI-MS analysis of the peptide digestion products of a LysK-Lyso fusion protein shows that all three lytic domains are active. In FIG. 5B the presence of the m/z 702 peak shows that both LysK domains are active. However, the peaks at m/z 645 ($A_2QKG_4$), 588 ($A_2QKG_3$), and 531 ($A_2QKG_2$) are the result of Gly-Gly cleavages by the Lysostaphin component of the fusion. Digestion with 390LysK-Lyso gives similar spectrums of peaks, with a less predominant peak at m/z 702. The peak at m/z 702 indicates that the predominant enzyme activity in LysK-Lyso construct is due to the LysK domains; the more evenly distributed peaks in the 390LysK-Lyso construct suggests the Lysostaphin endopeptidase domain is more active in this fusion.

Example 5

Turbidity Reduction Assay

The turbidity assay measures the drop in optical density ($OD_{600\,nm}$) resulting from lysis of the target bacteria with the phage endolysin-derived protein. The assay is performed in a Molecular Devices, Spectra Max 340 plate reader. The assay was modified from the cuvette method reported previously (Donovan et al., 2006b. *FEMS Microbiol. Lett.* 265: 133-139). *S. aureus* is grown to logarithmic phase ($OD_{600\,nm}$=0.4-0.6) at 37° C. in growth media (Tryptic Soy Broth, Brain Heart Infusion broth (BHI), or Meuller Hinton Broth) with shaking, harvested at 4° C. by centrifugation, and stored on ice until just before the assay when the cells are resuspended to $OD_{600\,nm}$=1.0 in 150 mM NaCl, 10 mM Tris HCl, pH 7.5 unless otherwise stated. Enzyme samples are added to three wells of a 96 well dish in 100 µl of buffer. All conditions are performed in triplicate wells. The assay is started by the addition, via multi channel pipettor, of 100 µl of cells resuspended in buffer. The cell suspensions are at sufficient concentration to reach an $OD_{600\,nm}$~1.0 when combined with the 100 µl of buffer/enzyme in the well. The "no enzyme control" contains buffer and cells, but no enzyme is included. $OD_{600\,nm}$ readings are taken automatically every 20 seconds. The readings for each well are transferred electronically to an Excel spreadsheet where they are analyzed in a sliding 40 second window over each group of 3 consecutive time points during the five minute period, to identify the highest instantaneous change in $OD_{600\,nm}$ for each well. The absolute values of $\Delta OD_{600\,nm}$ for each group of 3 time points is ranked for the entire 5 minute period. A plot of these values vs. time is examined for consistency (bubbles in the well cause high variability) and the highest consistent value is chosen. The highest value representing changes in the $OD_{600\,nm}$ in the control sample (cells alone) obtained the same way is then subtracted from the highest ranked $\Delta OD_{600\,nm}$ value for each experimental sample, and the 40 second values for the triplicate samples (wells) are averaged and multiplied by 1.5 to give a $\Delta OD_{600\,nm}$/minute. This value is then divided by the µg of enzyme protein in the sample to yield a specific activity $\Delta OD_{600\,nm}$/µg/min. pH Buffers: pH buffers were as follows: 10 mM sodium acetate buffer pH 5, 10 mM sodium acetate buffer pH 6, 10 mM Tris HCl buffer pH 7, 10 mM Tris HCl buffer pH 8, mM Tris HCl buffer pH 9, and 10 mM Carbonate buffer pH 10. Salt Buffers: Salt buffers were composed of 1% glycerol, 20 mM Tris pH 7.5 with varying NaCl from 0-500 mM. Storage Buffers: Storage buffers were composed of 400 mM NaCl, 1% glycerol, 20 mm Tris HCl pH 7.5 or with the addition of 1M trehalose, 2M proline, or 25% (final concentration) Glycerol.

Turbidity reduction assays were also performed with frozen cells. Live cells were grown to mid logarithmic phase ($OD_{600\,nm}$=0.4-0.6) at 37° C. in BHI with shaking, harvested at 4° C. by centrifugation, and stored on ice for 30 min to arrest growth. Cells were resuspended in 5 ml of buffer (150 mM NaCl, 10 mM Tris HCl, pH 7.5) per 250 ml of liquid culture. Glycerol was added to 20% (1.25 ml of 100% glycerol per 5 ml). The suspension was then separated into 1 ml aliquots and stored at −80° C. until needed. For turbidity assays, aliquots of cells were rapidly thawed by agitation in a room temperature water bath, pelleted by 16,000 g centrifugation, washed twice to remove residual glycerol, then resuspended in 150 mM NaCl, 10 mM Tris HCl, pH 7.5 or 300 mM NaCl, 10 mM Tris HCl, pH 7.5. Cell suspensions were then adjusted to concentration and used as in a standard turbidity reduction assay.

In the turbidity reduction assay (FIG. 4), the LysK-Lyso fusion is less active than Lysostaphin or LysK alone. However, removal of the LysK SH3b domain improves activity of the triple fusion lysin ~4 fold. This finding suggests that a phage endolysin's binding domain might inhibit antimicrobial activity, whereas the binding domain from a bacteriocin might make a better antimicrobial. Lysostaphin is a *S. simulans* bacteriocin; by definition, it is designed to kill all neighboring *S. aureus*. In contrast, LysK is predicted to have a strong binding constant in order to achieve lysis of just the host bacterial cell. Reversing the orientation of the LysK and Lysostaphin components of this triple domain fusion or inserting the 390LysK peptide into Lysostaphin does not appear to enhance the lytic activity in the turbidity reduction assay (390K-Lyso or 155Lyso-390LysK-LysoSH3b vs. Lyso-390K). Similarly, creating a hybrid dual domain lysine by removing the functional amidase domain (221K-Lyso) does not improve the level of lytic activity in this assay, over the 390K-Lyso fusion. Regardless of the levels of activity, it is important to note that all are functional fusions and are lytic for live cells.

All of the turbidity reduction assays were performed under optimal salt and pH conditions. To determine the optimal conditions for high antimicrobial activity, LysK-Lysostaphin had been tested in the turbidity reduction assay against live cells for pH optimum and NaCl concentrations. *S. aureus* 305 cells were resuspended in 20 mM Tris pH 7.5 containing 1% glycerol and NaCl concentrations ranging from 0-500 mM. The cells were treated with 10 µg of either C-His-LysK or Lysostaphin for 5 minutes in the turbidity reduction assay (FIG. 6). Lysostaphin activity is relatively unaffected by salt concentrations between 200 mM to 500 mM whereas LysK shows increasing activity from 150 mM with maximal activity at concentrations approaching 400 mM. LysK has a higher specific activity than Lysostaphin at NaCl concentrations greater than 150 mM. To determine the optimal pH, *S. aureus* 305 cells were resuspended in buffers ranging from pH 5 to pH 10 and treated with C-His-LysK or Lysostaphin for 5 minutes (FIG. 6). LysK and Lysostaphin show strong activity over a broad pH range from pH 6 to pH 9 (similar to previous reports for Lysostaphin (Schindler and Schuhardt. 1965. *Biochim. Biophys. Acta* 97: 242-250).

Each peptidoglycan hydrolase has unique salt and pH optima. When combined these optima are sometimes shifted with respect to their components. Removing the LysK SH3b cell wall binding domain from the LysK-Lyso fusion increases the activity of the fusion protein.

Example 6

Plate Lysis Assay

Due to the fact that antimicrobial assays for peptidoglycan hydrolases do not yield the same quantitative results between assays (Kusuma and Kokai-Kun. 2005. *Antimicrob. Agents Chemother.* 49(8): 3256-63), it was decided to test a second assay, namely, the plate lysis assay, with the fusion and parental proteins. Purified fusion enzymes were serially diluted into 150 mM NaCl, 10 mM tris, pH 7.5 buffer to yield concentrations of 10, 1, 0.1, and 0.01 µg/10 µl. 10 µl of each dilution was spotted onto TSB agar plates which were previously irrigated with 2 mL of mid-log (0.4-0.6 $OD_{600\,nm}$) *S. aureus* strain Newman, excess culture removed, and plates allowed to air dry at room temperature for ~30 minutes in a laminar flow hood. Enzyme spots are allowed to air dry and incubated overnight at 37° C.

The results of the plate lysis assay are shown in FIG. 7. As shown above in the turbidity reduction assay, all of the fusion constructs are able to kill live *S. aureus* in the plate lysis assay. As expected from the work of Kusuma and Kokai-Kun (supra), the relative activity levels differ from those observed in the turbidity reduction assay. The bacteriocin, Lysostaphin, shows the highest activity in the plate lysis assay, lysing cells at 0.01 µg. All other enzymes analyzed show a weaker but similar activity, requiring 0.1 µg to lyse the *S. aureus*. It should be noted that Lysostaphin is much smaller than the other proteins so in molar equivalents, there are ~3× as many Lysostaphin molecules as some of the other fusions e.g. LysK-Lyso (see FIGS. 2 and 3 for SDS gels and molecular weight comparisons). This might be contributing to the lack of quantitative identity between assays.

Example 7

Minimum Inhibitory Concentration

The Minimal Inhibitory Concentration (MIC) of fusion proteins with *S. aureus* Newman was determined. Enzymes are first serially diluted two fold across a 96 well plate from the first well containing 100 µl of buffer (150 mM NaCl, 10 mM tris, pH 7.5)+enzyme and 100 µl of 2× sterile Tryptic Soy Broth (TSB). 100 µl of these dilutions are then transferred to duplicate 96 well plates to which 100 µl of *S. aureus* Newman in TSB is added to each well. The CFU of the inoculating culture is ~5×10⁵ cells/ml. Plates are incubated 20 hours at 37° C., at which time plates are read with a 96 well plate reader and photographed. Plate reader $OD_{600\,nm}$ values are used to determine the MIC. Wells that have less than 50% $OD_{600\,nm}$ of the full growth (bright wells) are considered growth inhibited (red lines). Lysostaphin is serially diluted from 25 µg/ml, all other proteins are serially diluted from 125 µg/ml in the first well. Each well in the final assay contains 200 µl of 1×TSB with the buffer contributing 37.5 mM NaCl and 2.5 mM Tris.

MIC determinations for the fusion and parental lysins were performed in a 96 well microtiter plate (FIG. 8). Again, all of the fusion and parental lysins demonstrate the ability to inhibit *S. aureus* growth. Lysostaphin is again more active than the fusion proteins. Among the fusion proteins, the 221K-lyso construct is most active in the MIC assay, inhibiting culture growth at 5 µg/ml concentration.

Example 8

Bactericidal Blood Assays

Blood was taken from euthanized rats aseptically and immediately added to conical tubes containing heparin (5 U/ml). Heparinized rat blood was then stored rocking at room temperature until used. *S. aureus* mastitis strain 305 was grown to mid-log phase ($OD_{600\ nm}$=0.4-0.6) in Tryptic Soy Broth to ~100 cfu/µl. 1 µl of the diluted bacterial culture was added per 90 µls of heparinized rat blood en masse at a total volume sufficient to include for all samples. 455 µl of inoculated blood was then added to tubes containing 45 µl of each enzyme or buffer only (400 mM NaCl, 20 mM Tris HCl, 1% glycerol, pH 7.5). The final volume of enzyme and TSB inoculum were 9% and 1% of the final reaction volume, respectively. Reactions were incubated in a shaker at 37° C. between time points. Upon addition of blood, and at 90 and 180 minutes, aliquots were removed, diluted, and immediately plated onto TSB agar in triplicate. Plates were incubated at 37° C. overnight; colonies were then counted to determine the number of colony forming units per ml.

The results in FIG. 9 are presented as the % CFUs of the buffer alone control (no lysin added) and indicate that all of the LysK-Lyso fusions kill *S. aureus* in heparinized whole rat blood; therefore, the fusions should be active when applied systemically to cure septicemia and other tissue infections.

Example 9

Plate Lysis Assay for Testing Resistance Development

Cells were repeatedly exposed to peptidoglycan hydrolases over night on a tryptic soy agar (TSA) plate over a period of up to 20 days, similar to Loeffler et al. (2001, supra) with the following modifications. Lawns were prepared by diluting a mid log phase culture ($OD_{600\ nm}$ 0.4-0.6) of *S. aureus* Newman cells 1/20 in TSB, flooding a TSA plate with 2 mL of the culture dilution, incubating at room temperature for 1 minute, and removing the excess culture. The plates (with lids removed) were allowed to air dry in a laminar flow hood (∥30 minutes). Serial 10 fold dilutions of each enzyme in 150 mM NaCl, 10 mM Tris, pH 7.5 were prepared yielding five solutions ranging between 10 µg to 0.1 ng in 10 µl of each enzyme to be tested. Dilutions were spotted onto the lawn, allowed to air dry for 30 minutes, and incubated overnight at 37° C. Cells were scraped from the spot with the lowest concentration of enzyme where there was only partial clearing (some obvious lysis had occurred as indicated by partial clearing of the spot on the plate). These 'exposed' cells were used to inoculate 5 mL of TSB and grown for several hours to generate a new culture and subsequent lawn. Cells were exposed consecutively for up to 20 days, at which time cells were prepared and tested in turbidity reduction assays, as described previously. Each strain that resulted from repeated exposure to the peptidoglycan hydrolase construct was then tested against the hydrolase used in the selection procedure (and if a fusion, the parental hydrolases used to make the construct) to ascertain if any resistance to either the test construct or the hydrolases of origin had occurred as a result of repeated exposure.

The *S. aureus* strain Newman isolates resulting from the 10 day "resistant strain selection protocol" demonstrated nearly identical susceptibility, in the turbidity reduction assay, to both the parental lysins and the fusion constructs as the *S. aureus* strain Newman used to initiate the selection protocol. We conclude that there was no resistance development following repeated exposure to the lytic proteins.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant nucleic acid encoding an antimicrobial staphylococcal endolysin-lysostaphin triple fusion protein, comprising (1) an endolysin CHAP endopeptidase domain, (2) an endolysin amidase domain, and (3) a lysostaphin glycyl-glycine endopeptidase domain, wherein each domain of said fusion protein cuts the peptidoglycan cell wall at a different covalent bond of the peptidoglycan cell wall of live *Staphylococcus aureus* and said fusion protein has the sequence set forth in SEQ ID NO: 6, 8, 10, 12, or 14.

2. A construct comprising the nucleic acid of claim 1, wherein said nucleic acid is in operable linkage to a promoter that drives expression in a host cell.

3. A cloning vector comprising the construct of claim 2.

4. An expression vector comprising the construct of claim 2.

5. A process for transforming a host cell, comprising stably integrating the nucleic acid of claim 1 or the construct of claim 2 into the host cell.

6. An isolated host cell transformed with the nucleic acid according to claim 1.

7. An isolated host cell transformed with the construct according to claim 2.

8. The recombinant nucleic acid of claim 1 wherein said recombinant nucleic acid has the sequence set forth in SEQ ID NO: 5, SEQ ID NO: 7, SEQ ID NO:9, SEQ ID NO:11 or SEQ ID NO: 13.

9. The recombinant nucleic acid of claim 1 wherein each domain of said fusion protein has lytic activity in the presence of lytic activity of the other two domains.

10. A method of making a recombinant antimicrobial *Staphylococcus*—specified endolysin-lysostaphin triple fusion protein, said method comprising steps:
   a. introducing into a host cell a nucleic acid or construct encoding an antimicrobial *Staphylococcus*—specific endolysin-lysostaphin triple fusion protein wherein said fusion protein has the sequence set forth in SEQ ID NO: 6, 8, 10, 12, or 14;
   b. culturing said cell under conditions suitable for expression of said fusion protein; and
   c. recovering the fusion protein so expressed.

* * * * *